US011419800B2

(12) United States Patent
Mullen et al.

(10) Patent No.: US 11,419,800 B2
(45) Date of Patent: Aug. 23, 2022

(54) TOPICAL COMPOSITIONS CONTAINING ROSE OIL AND CANNABIDIOL AND METHODS OF MAKING AND USING THE SAME

(71) Applicant: JLABS Beauty LLC, Denver, CO (US)

(72) Inventors: Justine Mullen, Denver, CO (US); Anne Schlesselman Buthion, Denver, CO (US)

(73) Assignee: JLABS Beauty LLC, Denver, CO (US)

(*) Notice: Subject to any disclaimer, the term of this patent is extended or adjusted under 35 U.S.C. 154(b) by 0 days.

(21) Appl. No.: 16/952,641

(22) Filed: Nov. 19, 2020

(65) Prior Publication Data
US 2021/0169759 A1 Jun. 10, 2021

Related U.S. Application Data

(60) Provisional application No. 62/944,613, filed on Dec. 6, 2019.

(51) Int. Cl.
A61K 8/34 (2006.01)
A61K 47/36 (2006.01)
A61K 8/06 (2006.01)
A61K 8/37 (2006.01)
A61K 8/49 (2006.01)
A61K 8/9794 (2017.01)
A61K 8/73 (2006.01)
A61K 8/14 (2006.01)
A61Q 19/08 (2006.01)
A61P 17/10 (2006.01)
A61K 31/05 (2006.01)
A61K 36/738 (2006.01)
A61K 36/45 (2006.01)
A61K 9/00 (2006.01)
A61K 9/06 (2006.01)
A61K 9/127 (2006.01)
A61K 9/70 (2006.01)
A61K 8/02 (2006.01)
A61K 47/10 (2017.01)
A61K 47/14 (2017.01)
A61K 47/22 (2006.01)
A61K 47/46 (2006.01)
A61K 8/9789 (2017.01)

(52) U.S. Cl.
CPC ............ A61K 8/347 (2013.01); A61K 8/0212 (2013.01); A61K 8/062 (2013.01); A61K 8/14 (2013.01); A61K 8/345 (2013.01); A61K 8/375 (2013.01); A61K 8/498 (2013.01); A61K 8/735 (2013.01); A61K 8/9789 (2017.08); A61K 8/9794 (2017.08); A61K 9/0014 (2013.01); A61K 9/06 (2013.01); A61K 9/127 (2013.01); A61K 9/7007 (2013.01); A61K 31/05 (2013.01); A61K 36/45 (2013.01); A61K 36/738 (2013.01); A61K 47/10 (2013.01); A61K 47/14 (2013.01); A61K 47/22 (2013.01); A61K 47/36 (2013.01); A61K 47/46 (2013.01); A61P 17/10 (2018.01); A61Q 19/08 (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,087,445 A | 2/1992 | Haffey et al. |
| 5,100,660 A | 3/1992 | Hawe et al. |
| 6,492,326 B1 | 12/2002 | Robinson et al. |
| 8,685,446 B2 | 4/2014 | Casana-Giner et al. |
| 8,992,953 B2 | 3/2015 | Clavel et al. |
| 9,447,019 B2 | 9/2016 | Mechoulam et al. |
| 9,814,670 B2 | 11/2017 | Gan et al. |
| 2003/0206974 A1 | 11/2003 | Ilic et al. |
| 2004/0191330 A1 | 9/2004 | Keefe et al. |
| 2010/0015073 A1 | 1/2010 | Clavel et al. |
| 2011/0038949 A1 | 2/2011 | Oswal et al. |
| 2011/0064778 A1 | 3/2011 | Moser et al. |
| 2015/0320698 A1 | 11/2015 | Whalley et al. |
| 2016/0010126 A1 | 1/2016 | Poulos et al. |
| 2016/0235851 A1 | 8/2016 | Sand et al. |
| 2017/0008868 A1 | 1/2017 | Dialer et al. |
| 2017/0348276 A1 | 12/2017 | Bryson et al. |
| 2019/0031601 A1 | 1/2019 | ElSohly et al. |
| 2019/0142888 A1 | 5/2019 | Mojsa |
| 2019/0160393 A1 | 5/2019 | Marshall et al. |
| 2019/0231833 A1 | 8/2019 | Garti et al. |

FOREIGN PATENT DOCUMENTS

| | | |
|---|---|---|
| EP | 2578561 A1 | 4/2013 |
| WO | WO 02/24145 A2 | 3/2002 |
| WO | WO 2004/016277 A2 | 2/2004 |
| WO | WO 2008/010241 A1 | 1/2008 |
| WO | WO 2014/167557 A1 | 10/2014 |
| WO | WO 2017/139496 A1 | 8/2017 |
| WO | WO 2019/020738 A1 | 1/2019 |
| WO | WO 2019/113656 A1 | 6/2019 |
| WO | WO 2019/178360 A1 | 9/2019 |
| WO | WO 2019/198018 A1 | 10/2019 |

OTHER PUBLICATIONS

Ashtiani et al., "Liposomes in Cosmetics," J Skin Stem Cell. Sep. 2016; 3(3):e65815, 6 pages.

International Search Report and Written Opinion of the International Searching Authority for International Application No. PCT/US2020/061246 dated Feb. 10, 2021.

(Continued)

Primary Examiner — Nannette Holloman
(74) Attorney, Agent, or Firm — Cooley LLP

(57) ABSTRACT

The present disclosure provides compositions of rose oil, cannabidiol, and humectants and methods of using said compositions. The present disclosure also products containing the aforementioned products, including a face mask, a serum, a lotion, and an eye cream.

23 Claims, 1 Drawing Sheet

(56) References Cited

OTHER PUBLICATIONS

McClements, D.J., "Nanoemulsions versus microemulsions: terminology, differences, and similarities," Soft Matter, 2012, 8(6):1719-1729.

Montenegro, L., "Nanocarriers for skin delivery of cosmetic antioxidants," Journal of Pharmacy & Pharmacognosy Research, 2014, 2(4), 73-92.

Nohynek et al., "Grey Goo on the Skin? Nanotechnology, Cosmetic and Sunscreen Safety," Critical Reviews in Toxicology. 37:251-277, 2007.

Patravale et al., "Novel cosmetic delivery systems: an application update," International Journal of Cosmetic Science, 2008, 30, 19-33.

Schürch et al., "Potential of plant cells in culture for cosmetic application," Phytochern Rev (2008) 7:599-605.

Zamboni, W.C., "Concept and Clinical Evaluation of Carrier-Mediated Anticancer Agents," The Oncologist, 2008; 13:248-260.

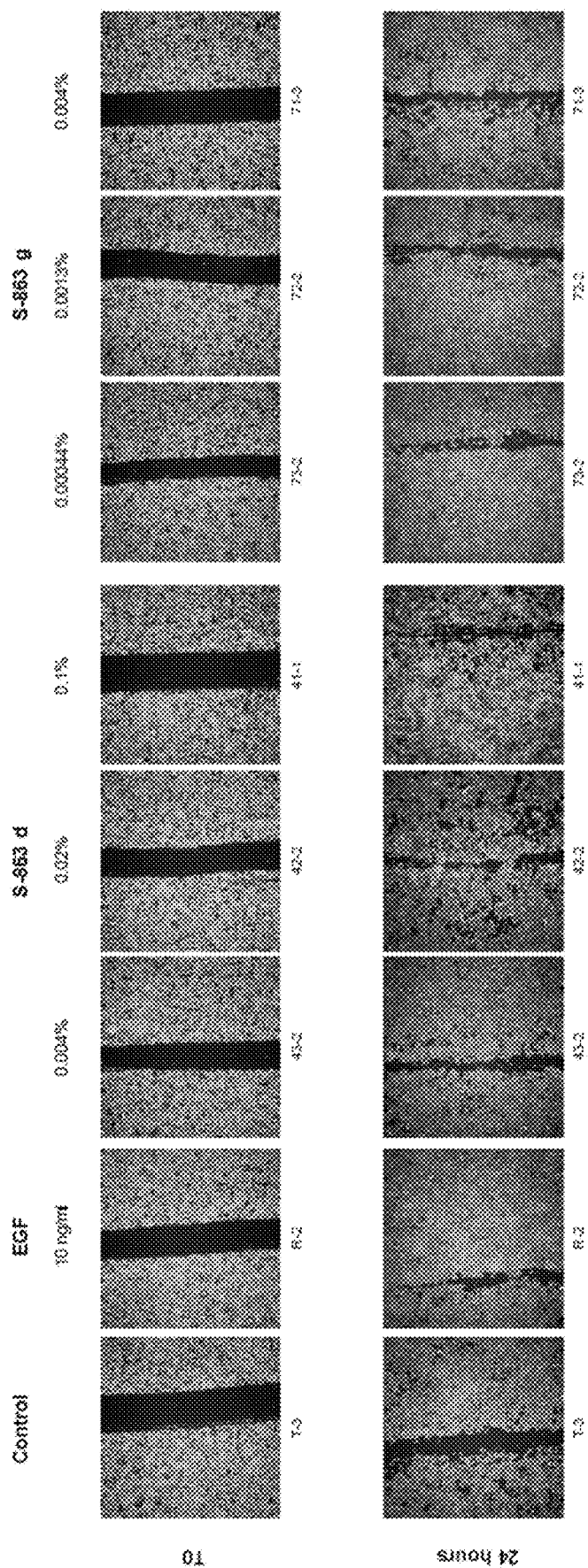

TOPICAL COMPOSITIONS CONTAINING ROSE OIL AND CANNABIDIOL AND METHODS OF MAKING AND USING THE SAME

CROSS-REFERENCE TO RELATED APPLICATIONS

This application claims priority to U.S. Provisional No. 62/944,613, filed Dec. 6, 2019, the content of which is incorporated by reference herein in its entirety.

FIELD

The disclosure relates to compositions containing cannabidiol and rose oil. The resulting compositions can be used in skin care products, such as lotions, serums, eye creams, or face masks. The disclosure further relates to methods of applying such products.

BACKGROUND OF THE INVENTION

Aging, chronic exposure to adverse environmental factors, malnutrition, puberty, and fatigue can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult, include a general reduction in cellular and tissue vitality, reduction in cell replication rates, reduced cutaneous blood flow, reduced moisture content, alterations in regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Many skin care compositions cause side effects, such as irritation, dermatitis, and acne. Therefore, there remains a need in the art in the cosmetics industry to develop skin care compositions, which positively affect skin health.

SUMMARY OF THE INVENTION

Topical compositions containing rose oil and cannabidiol and methods of making the same are described herein.

In some aspects, the present disclosure provides a topical skin care composition comprising: (i) rose oil; (ii) cannabidiol (CBD), and (iii) a humectant, wherein the composition is delivered to skin by a cosmetic vehicle.

In some embodiments, the topical skin care composition comprises up to about 5 rose oil and up to about 2% CBD.

In some embodiments, the topical skin care composition comprises up to about 2% of a humectant.

In some embodiments, the topical skin care composition comprises a humectant selected from the group consisting of *Aloe vera* extract, glyceryl glucoside, and hyaluronic acid.

In some embodiments, the topical skin care composition comprises a humectant, wherein the humectant is hyaluronic acid.

In some embodiments, the topical skin care composition comprises a humectant, wherein the humectant is glyceryl glucoside.

In some embodiments, the topical skin care composition comprises rose oil, wherein the rose oil is an extract of *Rhododendron ferrugineum*.

In some embodiments, the topical skin care composition comprises rose oil, wherein the rose oil is an extract of *Rhododendron ferrugineum*, and wherein the extract comprises stem cells.

In some embodiments, the topical skin care composition comprises rose oil, wherein the rose oil is an extract of *Rosa damascena*.

In some embodiments, the topical skin care composition comprises a cosmetic vehicle, wherein the cosmetic vehicle is selected from the group consisting of liposome, nanosome, oil-in-water emulsion, and water-in-oil emulsion.

In some embodiments, the topical skin care composition comprises a cosmetic vehicle, wherein the cosmetic vehicle is a nanosome.

In some embodiments, the topical skin care composition comprises a cosmetic vehicle, wherein the cosmetic vehicle is a nanosome, wherein the nanosome has an average particle size of 90 nm.

In some embodiments, the topical skin care composition comprises a cosmetic vehicle, wherein the cosmetic vehicle is an oil-in-water emulsion.

In some embodiments, the topical skin care composition comprises a cosmetic vehicle, wherein the cosmetic vehicle comprises up to about 60% glycerin, up to about 15% caprylic/capric triglycerides, and up to about 3% phospholipids.

In some embodiments, the topical skin care compositions of the present invention further comprise tocopherol.

In some aspects, the present disclosure provides a method of applying a topical skin care composition to skin, comprising topically applying the topical skin care composition, wherein the topical skin composition comprises (i) rose oil; (ii) cannabidiol (CBD), and (iii) a humectant.

In some aspects, the present disclosure provides a method of applying a topical skin care composition to skin, wherein the composition is applied to a face.

In some aspects, the present disclosure provides a method of applying a topical skin care composition to skin, wherein the composition is applied to a wrinkle.

In some aspects, the present disclosure provides a method of applying a topical skin care composition to skin, wherein the composition is applied to a fine line.

In some aspects, the present disclosure provides a method of reducing acne comprising applying the topical skin care composition comprising (i) rose oil; (ii) cannabidiol (CBD), and (iii) a humectant to the skin In some embodiments, the present disclosure provides a kit comprising a topical skin composition of the present invention combined with a dispensing component for the topical skin composition, packaging for the dispensing component, and instructions for using the dispenser and topical skin composition.

In some embodiments, the present disclosure provides a topical skin composition comprising (i) rose oil; (ii) cannabidiol (CBD), and (iii) a humectant, wherein the composition is incorporated into a product selected from the group consisting of an eye cream, a serum, a face mask, and a lotion.

In some embodiments, the present disclosure provides products selected from the group consisting of an eye cream, a serum, a face mask, and a lotion, wherein a topical skin care composition comprising (i) rose oil; (ii) CBD, and (iii) a humectant is incorporated into any one of said products.

In some embodiments, provided herein is a topical skin care composition comprising 2% v/v rose oil, 1% w/v CBD, 54% v/v glycerin, 1% v/v hyaluronic acid, 0.1% v/v tocopherol, 3% v/v phospholipids, and 10% v/v caprylic/capric triglycerides, wherein the rose oil is an extract from *Rhododendron ferrugineum*.

In some embodiments, provided herein is a topical skin care composition comprising 2% v/v rose oil, 1% v/v CBD, 54% v/v glycerin, 1% v/v hyaluronic acid, 0.1% v/v tocopherol, 3% v/v phospholipids, and 10% v/v caprylic/capric triglycerides, wherein the rose oil is an extract from *Rhododendron ferrugineum*.

In some embodiments, provided herein is a topical skin care composition comprising 2% v/v rose oil, 1% w/v CBD, 54% v/v glycerin, 1% v/v hyaluronic acid, 3% v/v phospholipids, and 10% v/v caprylic/capric triglycerides, wherein the rose oil is an extract from *Rhododendron ferrugineum*.

In some embodiments, provided herein is a topical skin care composition comprising 2% v/v rose oil, 1% v/v CBD, 54% v/v glycerin, 1% v/v hyaluronic acid, 3% v/v phospholipids, and 10% v/v caprylic/capric triglycerides, wherein the rose oil is an extract from *Rhododendron ferrugineum*.

DESCRIPTION OF THE DRAWINGS

FIG. 1 shows representative images of the effect of compounds S-863d and S-863g on the migration of KSCs.

DETAILED DESCRIPTION OF THE INVENTION

Definitions

As used herein, the verb "comprise" is used in this description and in the claims and its conjugations are used in its non-limiting sense to mean that items following the word are included, but items not specifically mentioned are not excluded.

As used herein, the term "about" refers to plus or minus 10% of the referenced number unless otherwise stated or otherwise evident by the context, and except where such a range would exceed 100% of a possible value, or fall below 0% of a possible value, such as less than 0% content of an ingredient, or more than 100% of the total contents of a composition. For example, reference to an absolute content of cannabidiol of "about 1% w/w" means that cannabidiol can be present at any amount ranging from 0.9% to 1.1% content by weight.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the term "skin" refers to any of the layers of the skin, including the epidermis, dermis, and hypodermis. The epidermis has five sub-layers, including the stratum corneum, stratum lucidum, stratum granulosum, stratum spinosum, and stratum basale, which are listed from the outermost sub-layer to the innermost sub-layer. For example, the stratum corneum is the skin's surface.

As used herein, the term "skin care composition" refers to any formulation that is applied to the skin.

Various concentration expressions, including volume concentrations, weight concentrations, and mass concentrations, are utilized to describe the percentage of a component in a solution. Volume concentration has units of % v/v, where v/v is volume per volume. If a solution contains κ% v/v of a component, 5 mL of the component is in a total solution of 100 mL. Weight concentration of a solution is expressed as % w/w, where w/w is weight per weight. If a solution contains 30% w/w of sodium chloride, the solution contains 30 g of sodium chloride and 70 g of solvent. Mass concentration of a solution is expressed as % w/v, where w/v is weight per volume. If 1 g of sodium chloride is dissolved in a solution with a total volume of 100 mL, a 1% w/v sodium chloride solution has been made.

In some embodiments, the disclosure describes "topical application" of the skin care composition. As defined herein, "topical application" is application of a composition to the skin.

As used herein, the term "cosmetic vehicle" refers to any molecule, group of molecules, or biomolecule used to deliver ingredients of the skin composition to the skin. Ingredients may be active ingredients or additional ingredients described herein. Non-limiting examples of cosmetic vehicles include liposomes, nanosomes, emulsions, microemulsions, nanocapsules, solid lipid nanoparticles, and nanocrystals.

In some embodiments, the skin care compositions contain humectants. As used herein, the term "humectant" refers to a hygroscopic substance, which moisturizes the skin. Non-limiting examples of humectants are provided throughout the disclosure.

The disclosure provides plant parts. As used herein, the term "plant part" refers to any part of a plant including but not limited to the embryo, shoot, root, stem, seed, stipule, leaf, petal, flower, inflorescence, bud, ovule, bract, trichome, branch, petiole, internode, bark, pubescence, tiller, rhizome, frond, blade, pollen, stamen, mesocarp, epicarp, endosperm, spermoderm, disk, embryo, and the like. The two main parts of plants grown in some sort of media, such as soil or vermiculite, are often referred to as the "above-ground" part, also often referred to as the "shoots", and the "below-ground" part, also often referred to as the "roots".

Unless otherwise noted, references to cannabidiol (CBD) in the present disclosure should be understood as references to both the acidic (CBDA) and decarboxylated (CBD) versions of the cannabidiol. For example, references to CBD should be understood as references to the combined CBD and CBDA content, accounting for weight loss during decarboxylation.

In some embodiments, the compositions contain cannabidiol (CBD). As used herein, CBD refers to synthetic CBD or to a *Cannabis* extract, which contains between 1% w/w to 100% w/w CBD. In some embodiments, pure CBD is utilized in the compositions of the disclosure. As used herein, pure CBD refers to synthetic CBD or a CBD extract, which contains between about 80% w/w to about 100% w/w CBD.

As used herein, regulating a skin condition includes delaying, minimizing, effacing, or preventing visible or tactile discontinuities in skin or both visible and tactile discontinuities in the skin (e.g., texture irregularities in the skin which may be detected visually or by feel), including signs of skin aging.

Skin Care Compositions

In some embodiments, the disclosure provides skin care compositions. Skin care compositions contain active ingredients and optionally contain additional ingredients, which are described below. In some embodiments, the skin care compositions are delivered by a cosmetic vehicle topically to the skin. In some embodiments, the skin care compositions are incorporated into products as described throughout this disclosure. In some embodiments, the invention provides luxury and designer skin care products enriched with CBD and rose oil.

In some embodiments, the disclosure provides skin care compositions that are Halal certified.

In some embodiments, the disclosure provides skin care compositions that do not contain any substances that are carcinogenic, mutagenic or toxic for reproduction.

In some embodiments, the disclosure provides skin care compositions that do not contain any allergenic substances according to the applicable governmental regulations for cosmetics.

In some embodiments, the disclosure provides skin care compositions that are not subjected to an irradiation step.

In some embodiments, the disclosure provides skin care compositions for which their development and/or manufacturing did not involve the use of any animal originating and/or animal derived components.

In some embodiments, the disclosure provides skin care compositions that do not contain any ingredients subject to the Nagoya Protocol.

Active Ingredients

The present disclosure teaches various skin compositions containing one or more active ingredients. In some embodiments, the active ingredients are rose oil, cannabidiol, and a humectant.

In some embodiments, the present disclosure teaches skin compositions containing up to 5% w/v CBD, up to 5% v/v rose oil, and up to 5% v/v of a humectant. In some embodiments, the present disclosure teaches skin compositions containing up to 5% v/v CBD, up to 5% v/v rose oil, and up to 5% v/v of a humectant. In some embodiments, the present disclosure teaches skin compositions containing 1% w/v CBD, 2% v/v rose oil, and 1% v/v humectant. In some embodiments, the present disclosure teaches skin compositions containing 1% v/v CBD, 2% v/v rose oil, and 1% v/v humectant. In some embodiments, the present disclosure teaches skin compositions containing 1% w/w CBD, 2% v/v rose oil, and 1% v/v humectant.

Rose Oil

In some embodiments, the present disclosure teaches compositions that contain the active ingredient rose oil. In some embodiments, rose oil causes pain relief, reduces anxiety, reduces stress, eases depression, reduces acne, and exhibits anti-bacterial and anti-fungal properties.

In some embodiments, the compositions of the disclosure contain about 0% to about 5 rose oil. In some embodiments, the compositions contain up to about 0.5%, or up to about 1%, or up to about 1.5%, or up to about 2.0%, or up to about 2.5%, or up to about 3.0%, or up to about 3.5%, or up to about 4.0%, or up to about 4.5%, or up to about 5% rose oil.

In some embodiments, rose oil is an extract from a plant selected from the group consisting of *Rosa damascena, Rosa centifolia, Rhododendron ferrugineum, Rhododendron brachycarpum, Rosa gallica, Rosa gallica* Linne, *Rosa gallica* var. *aegyptiaca*, and *Rhododendron hirsutum*. In some embodiments, rose oil is an extract of *Rosa damascena*. In some embodiments, rose oil is an extract of *Rhododendron ferrugineum*.

In some embodiments, rose oil is a plant meristematic stem cell extract from *Rosa damascena, Rosa centifolia, Rosa gallica, Rosa gallica* Linne, *Rosa gallica* var. *aegyp-* *tiaca, Rhododendron ferrugineum, Rhododendron brachycarpum,* or *Rhododendron hirsutum*. Meristematic stem cells are undifferentiated cells serving as the origin of plant vitality, as they maintain themselves while providing a steady supply of precursor cells to form differentiated tissues and organs in plants. Plant meristematic cells contain epigenetic factors similar to those of adult human stem cells. Methods of making plant meristematic cell extracts are found in International Publication No. 2014/167557 (published Oct. 16, 2014), which is incorporated by reference herein in its entirety.

In some embodiments, rose oil is selected from the group consisting of a meristematic stem cell extract from *Rhododendron ferrugineum*, Alp Rose (Mibelle Biochemistry), AlpineRoseActive™ (Mibelle Biochemistry), and Rose Absolute.

In some embodiments, rose oil is used in combination with an alternative plant extract. In some embodiments, rose oil is replaced with an alternative plant extract. In some embodiments, the alternative plant extract contains stem cells. Non-limiting examples of plant extracts are selected from the group consisting of *Bellis perrenis, Leontopodium alpinum, Malus domestica, Catharanthus roseus, Catharanthus tincorius, Eriodictyon californicum, Camellia sinensin, Marrubium vulgare, Schinus molle, Camellia japonica, Schisandar chinensin, Oenothera biennis, Menyanthes trifoliate, Michelia magnifica, Xylosma japonicum, Prunus cerasifera, Nyssa sinensis, Chimonanthus praecox, Sassafras tzumu, Inula helianthus-aquatica, Capparis bodinieri, Passiflora caerulea, Galium aparine, Boehmeria platyphylla, Colquhounia coccinea, Sageretia rugosa, Jasminum stephanense, Antirrhinum majus, Daphniphyllum oldhamii, Cuscuta chinensis, Salix variegate, Osmanthus parvifolius, Euphorbia trigona, Calliandra haematocephala, Excoecaria acerifolia, Dianthus chinensis, Myriophyllum spicatum, Nymphoides peltatum, Prunus salicina, Solanum coagulans, Elaeis guineensis, Rhododendron moulmainense, Spatholobus suberectus, Artabotrys hexapetalus, Hibiscus syriacus, Lonicera calcarata, Hydnocarpus hainanensis, Ilex fragilis, Antidesma venosum, Acacia pennata* ssp. *Kerrii, Althaea rosea, Millettia velutina, Themeda japonica, Dalbergia hancei, Ipomoea batatas, Photinia glomerata, Hippophae rhamnoides, Azadirachta indica, Karelinia caspica, Bauhinia touranensis, Eriobotrya japonicas, Anaphalis contorta,* and *Cratoxylum prunifolium*.

In some embodiments, AlpineRoseActive™ is used in the compositions of the disclosure. AlpineRoseActive™ is an extract of *Rhododendron ferriguneum*. AlpineRoseActive™ is not an aromatic oil. This extract protects exerts an antiviral effect against herpes simplex and protects against protein oxidation.

In some embodiments, rose oil is replaced with daisy plant extract. In some embodiments, rose oil is used in addition to a daisy plant extract. Non-limiting examples of daisy plant extracts are selected from the group consisting of *Bellis perennis, Leucanthemum vulgare,* and *Chrysanthemum leucanthemum*.

In some embodiments, rose oil is replaced with orchid extracts. In some embodiments, rose oil is used in addition to an orchid extract. In some embodiments, the orchid extracts contain stem cells. Non-limiting examples of orchid extracts are selected from the group consisting of *Calanthe discolor, Vanda coeurela, Papillionanthes teres,* and *Vanda denisoniona*. In some embodiments, a product containing orchid extract from *Calanthe discolor*, ORCHISTEM™, is included in the compositions of the disclosure. In some embodiments, orchid extracts increase cell to cell communication, stimulate epidermal growth factor, and increase elastin and collagen production in skin.

In some embodiments, rose oil or an alternative plant extract is produced according to known methods in the art. The extract can be from the whole plant or plant parts (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, or water.

Cannabidiol

In some embodiments, the present disclosure teaches products that contain the active ingredient cannabidiol. In some embodiments, cannabidiol is extracted from Cannabis plants to form a CBD extract. Non-limiting examples of Cannabis plants include Cannabis sativa, Cannabis indica, or Cannabis ruderalis. In some embodiments, cannabidiol is extracted from hybrid varieties of Cannabis. Cannabidiol is extracted from Cannabis plants according to known methods in the art. Non-limiting extraction methods include sonication, heating under reflux, soxhlet extraction, solid-phase micro-extraction, supercritical-fluid extraction, pressurized-liquid extraction, microwave-assisted extraction, solid-phase extraction, and surfactant-mediated techniques. In some embodiments, the steps for extraction include, but are not limited, to pre-washing, drying of plant parts or freeze drying, and grinding to obtain homogenous extracted plant samples.

In some embodiments, cannabidiol is extracted using an alcohol-based extraction. In some embodiments, cannabidiol is extracted with ethanol. In some embodiments, cannabidiol is obtained using a supercritical carbon dioxide based extraction. Methods for extraction of CBD from Cannabis plants are described in the following patent documents which are incorporated by reference in their entirety herein: U.S. Publication No. 2019/0231833 A1, (published Aug. 1, 2019), International Publication No. 2019/020738 (published Jan. 31, 2019), International Publication No. 2004/016277 A1 (published Feb. 26, 2004), and U.S. Publication No. 2019/0160393 A1 (published May 30, 2019).

In some embodiments, the compositions of the disclosure use CBD extracts. In some embodiments, a CBD extract contains from about 1% w/w to about 100% w/w of CBD. In some embodiments, the CBD extract contains about 1% w/w CBD, or about 2% w/w CBD, or about 3% w/w CBD, or about 4% w/w CBD, or about 5% w/w CBD, or about 10% w/w CBD, or about 20% w/w CBD, or about 30% w/w CBD, or about 40% w/w CBD, or about 50% w/w CBD, or about 60% w/w CBD, or about 70% w/w CBD, or about 80% w/w CBD, or about 90% w/w CBD, or about 95% w/w CBD, or about 96% w/w CBD, or about 97% w/w CBD, or about 98% w/w CBD, or about 99% w/w CBD, or about 100% w/w CBD. In some embodiments, the CBD extract contains about 99.3% w/w CBD.

In some embodiments, CBD or a CBD extract is produced from the whole Cannabis plant. In some embodiments, CBD or a CBD extract is produced from the above-surface plant parts of Cannabis plants. The above-surface plant parts are also known as plant tops, above ground plant parts and plant shoots. The shoots of plants generally refer to a plant's stems, leaves, flowers and fruit. In some embodiments, CBD or a CBD extract is produced from one or more Cannabis plant parts (e.g., root, bark, sap, stem, leaf, flower, seed, leaf, stem, root, flower, seed, sap, bark, etc.). In some embodiments, CBD or CBD extract is produced from Cannabis flowers. In some embodiments, CBD or CBD extract is produced from the stems and leaves of a Cannabis plant.

In some embodiments, the CBD extract is CBD Isolate Max™ (Kazmira™).

In some embodiments, CBD extracts contain one or more cannabinoids. Non-limiting examples of cannabinoids include cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), and Tetrahydrocannabinol (THC), cannabidiolic acid (CBDA), and tetrahydrocannabinolic acid (THCA).

In some embodiments, the CBD extract contains CBDV. In some embodiments, the CBD extract contains between about 0% w/w and about 5% w/w CBDV. In some embodiments, the CBD extract contains between about 0.1% w/w and about 5% w/w CBDV. In some embodiments, the CBD extract contains about 0.10% w/w, about 0.15% w/w, about 0.19% w/w, about 0.20% w/w, about 0.25% w/w, about 0.30% w/w, about 0.35% w/w, about 0.40% w/w, about 0.45% w/w, about 0.5% w/w, about 0.6% w/w, about 0.7% w/w, about 0.8% w/w, about 0.9% w/w, about 1.0% w/w, about 1.5% w/w, about 2.0% w/w, about 2.5% w/w, about 3.0% w/w, about 3.5% w/w, about 4.0% w/w, about 4.5% w/w, or about 5.0% w/w CBDV.

In some embodiments, the CBD extract contains one or more terpenes. Terpenes are a class of compounds composed of five-carbon isoprene units that have the molecular formula $(C_5H_8)_n$, where n dictates the number of isoprene units. Non-limiting examples of terpenes include alpha-cedrene, alpha-humulene, alpha-pinene, alpha-terpinene, beta-myrcene, beta-pinene, borneol, camphene, camphor, caryophyllene oxide, cedrol, alpha-bisabolol, alpha-phellandrene, isopulegol, cis-nerolidol, 3-carene, fenchyl alcohol, hexahydrothymol, eucalyptol, isoborneol, farnesene, fenchone, gamma-terpinene, geraniol, geranyl acetate, humulene, guaiol, limonene, linalool, nerol, ocimene, alpha-phellandrene, pulegone, sabinene, sabinene hydrate, terpineol, terpinolene, trans-caryophyllene, β-caryophyllene, trans-nerolidol, and valencene. In some embodiments, the CBD extract contains trans-nerolidol. In some embodiments, the CBD extract contains alpha-bisabolol. In some embodiments, the CBD extract contains linalool. In some embodiments, the CBD extract contains β-caryophyllene. In some embodiments, the CBD extract contains guaiol. In some embodiments, the CBD extract contains humulene. In some embodiments, the CBD extract contains limonene. In some embodiments, the CBD extract contains alpha-phellandrene.

In some embodiments, the CBD extract contains less than about 1.0% w/w terpenes. In some embodiments the CBD extract contains less than about 0.01% w/w, about 0.02% w/w, about 0.03% w/w, about 0.04% w/w, about 0.05 w/w, about 0.06% w/w, about 0.07% w/w, about 0.08% w/w, about 0.09% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1.0% w/w terpenes.

In some embodiments, cannabidiol is produced synthetically. As described herein, synthetic cannabidiol includes CBD analogs, CBD salts, modified CBD, and propyl cannabinoids (CBDv). Synthetic CBD has the same or similar therapeutic effects as naturally occurring CBD when administered to the subjects. Patent documents, such as U.S. Publication No. 2019/0031601 (published Jan. 31, 2019), U.S. Pat. No. 9,447,019 (issued Sep. 20, 2016), and U.S. Publication No. 2015/0320698 (published Nov. 12, 2015), which describe synthetic cannabinoids are incorporated by reference herein in their entirety.

Methods for cannabidiol synthesis are described in the following patent documents, which are incorporated by reference in their entirety herein: EP Publication No. 2578561 A1 (published Apr. 10, 2013), U.S. Publication No. 2017/0008868 A1 (published Aug. 28, 2018). In some embodiments, cannabidiol is produced in microorganisms. Methods for producing cannabidiol in microorganisms are described in U.S. Publication No. 2016/0010126 A1 (published Jan. 14, 2016) and International Publication No. 2017/139496 (published Aug. 17, 2016), which are incorporated by reference in their entireties, herein. In some embodiments, CBD is obtained from commercial sources such as Bluebird Botanicals, CBDistillery™, or ExtractLabs™.

In some embodiments, a CBD extract or synthetic CBD is pure CBD. In some embodiments, pure CBD contains from about 80% w/w to about 100% w/w of CBD. In some embodiments, pure CBD contains about 80% w/w, or about 85 w/w, or about 90% w/w, or about 95% w/w, or about 96% w/w, or about 97% w/w, or about 98% w/w, or about 99% w/w, or about 100% w/w CBD.

In some embodiments, the compositions of the disclosure contain cannabidiolic acid (CBDA) in addition to CBD. In some embodiments, CBDA is converted to CBD by decarboxylation according to the reaction below:

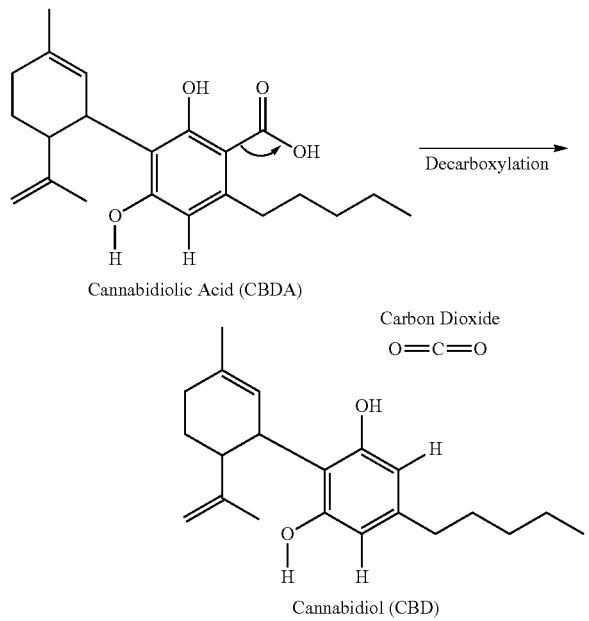

In some embodiments, CBD is obtained from CBDA by heating CBDA to temperatures above 270° F.

In some embodiments, the resultant CBD extracts are processed to remove unwanted co-extracted plant material and phytochemicals, and/or to remove THC.

In some embodiments, the CBD used in the compositions of the disclosure is isolated as a crystalline solid.

In some embodiments, the CBD used in the compositions of the disclosure is tested for confirmation and certification as to its purity and/or as being free from certain contaminants.

In some embodiments, the CBD used in the compositions of the disclosure are tested for one or more of residual solvents or other impurities.

In some embodiments, farm-to-product traceability is employed throughout the entirety of the processes utilized to grow, harvest, extract and purify the CBD used in the compositions of the disclosure.

In some embodiments, the compositions of the disclosure contain from about 0% w/w to about 5% w/w CBD. In some embodiments, the compositions of the disclosure contain from about 0.1% w/w to about 5% w/w CBD. In some embodiments, the CBD is an extract. In some embodiments, the CBD is synthetic. In some embodiments, the compositions contain up to about 0.5% w/w, or up to about 1% w/w, or up to about 1.5% w/w, or up to about 2.0% w/w, or up to about 2.5% w/w, or up to about 3.0% w/w, or up to about 3.5% w/w, or up to about 4.0% w/w, or up to about 4.5% w/w, or up to about 5% w/w CBD.

In some embodiments, the compositions of the disclosure contain from about 0% w/v to about 5% w/v CBD. In some embodiments, the compositions of the disclosure contain from about 0.1% w/v to about 5% w/v CBD. In some embodiments, the CBD is an extract. In some embodiments, the CBD is synthetic. In some embodiments, the compositions contain up to about 0.5% w/v, or up to about 1% w/v, or up to about 1.5% w/v, or up to about 2.0% w/v, or up to about 2.5% w/v, or up to about 3.0% w/v, or up to about 3.5% w/v, or up to about 4.0% w/v, or up to about 4.5% w/v, or up to about 5% w/v CBD.

In some embodiments, the compositions of the disclosure contain from about 0 v/v to about 5% v/v CBD. In some embodiments, the compositions of the disclosure contain from about 0.1% v/v to about 5% v/v CBD. In some embodiments, the CBD is an extract. In some embodiments, the CBD is synthetic. In some embodiments, the compositions contain up to about 0.5% v/v, or up to about 1% v/v, or up to about 1.5% v/v, or up to about 2.0% v/v, or up to about 2.5% v/v, or up to about 3.0% v/v, or up to about 3.5% v/v, or up to about 4.0% v/v, or up to about 4.5% v/v, or up to about 5% v/v CBD.

Cannabidiol is associated with several health benefits. Examples include pain relief and reduction of anxiety, depression, insomnia, migraines, and acne.

The high lipophilicity of CBD (structure shown below) makes delivery of this compound to the skin challenging.

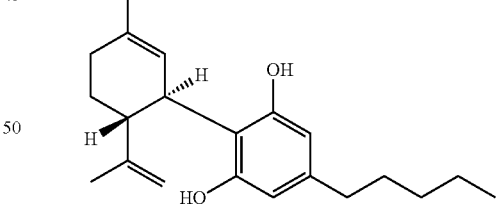

In some embodiments, the compositions described in the present disclosure allow accumulation of CBD in the skin.

Humectants

In some embodiments, the present disclosure teaches compositions that contain a humectant as an active ingredient. In some embodiments, humectants cause increased elasticity, smoothness, and hydration of the skin. In some embodiments, the humectant glyceryl glucoside (Glycoin®) is used in the products of the disclosure. In some embodiments, glyceryl glucoside is isolated from *Myrothamnus flabellifolia* or *Spirulina*. Glyceryl glucoside is a multifunctional anti-aging and cell-boosting ingredient. Glyceryl glucoside stimulates aged skin cells by boosting and revitalizing their metabolic activity, and stimulating ATP synthesis and anti-oxidant activity. In some embodiments, the compositions of the disclosure contain about 0% v/v to about 5% v/v glyceryl glucoside. In some embodiments, the compositions contain up to about 0.5% v/v, or up to about 1% v/v, or up to about 1.5% v/v, or up to about 2.0% v/v, or up to about 2.5% v/v, or up to about 3.0% v/v, or up to about 3.5% v/v, or up to about 4.0% v/v, or up to about 4.5% v/v, or up to about 5% v/v glyceryl glucoside. In some embodiments, glyceryl glucoside in the compositions of the disclosure stimulates cell renewal, growth factors and ATP synthesis. In some embodiments, glyceryl glucoside in the compositions of the disclosure boosts anti-oxidative enzymes. Non-limiting examples of anti-oxidative enzymes include superoxide dismutase 1 (SOD1), superoxide dismutase 2 (SOD2), and catalase (CAT). In some embodiments, glyceryl glucoside in the compositions of the disclosure increases hydration of the skin. In some embodiments, glyceryl glucoside in the compositions of the disclosure increases skin elasticity, skin smoothness, skin thickness, and combinations thereof. In some embodiments, glyceryl glucoside reduces sunburn and skin redness. In some embodiments, glyceryl glucoside causes whitening and lightening of pigmented skin. In some embodiments, glyceryl glucoside stimulates tissue repair and wound healing.

In some embodiments, the present disclosure teaches compositions that contain the humectant hyaluronic acid. Hyaluronic acid promotes hydration and can hold up to 1000 times its weight in water. Hyaluronic acid is a glycosaminoglycan which is used to prevent aging, including wrinkles around the eyes. In some embodiments, the compositions of the disclosure contain about 0% v/v to about 5% v/v hyaluronic acid. In some embodiments, the compositions contain up to about 0.5% v/v, or up to about 1% v/v, or up to about 1.5% v/v, or up to about 2.0% v/v, or up to about 2.5% v/v, or up to about 3.0% v/v, or up to about 3.5% v/v, or up to about 4.0% v/v, or up to about 4.5% v/v, or up to about 5% v/v hyaluronic acid. In some embodiments, the compositions of the disclosure contain hyaluronic acid, which is released over time. In some embodiments, hyaluronic acid is released over 48 hours or more. In some embodiments, hyaluronic acid is provided as Hyalusphere™. Hyalusphere™ is a high molecular weight hyaluronic acid. In some embodiments, the compositions of the disclosure contain Hyalusphere™, which is released over time. In some embodiments, Hyalusphere™ is released over 48 hours or more. In some embodiments, hyaluronic acid is used in creams or lotions, including but not limited to face cream and eye cream. In some embodiments, hyaluronic acid is not used with oils. In some embodiments, a hyaluronic acid derivative is used as a humectant. In some embodiments, PrimalHyal™ is used as a humectant. PrimalHyal™ is resistant to hyaluronidases and penetrates twice as deep into the skin as hyaluronic acid.

In some embodiments, the present disclosure teaches compositions that contain an extract of *Aloe vera* as a humectant. In some embodiments, about 0% v/v to about 5% v/v of the composition contains *Aloe vera* extract. In some embodiments, the compositions contain up to about 0.5% v/v, or up to about 1% v/v, or up to about 1.5% v/v, or up to about 2.0% v/v, or up to about 2.5% v/v, or up to about 3.0% v/v, or up to about 3.5% v/v, or up to about 4.0% v/v, or up to about 4.5% v/v, or up to about 5% v/v *Aloe vera* extract.

In some embodiments, alternative humectants are used in the products of the disclosure. Non-limiting examples of humectants include amino acids, chondroitin sulfate, diglycerol, erythritol, fructose, glucose, glycerol, glycerol polymers, glycol, 1,2,6-hexanetriol, honey, hyaluronic acid, hydrogenated honey, hydrogenated starch hydrolyzate, inositol, lactitol, maltitol, maltose, mannitol, natural humectant factor, PEG-15-butanediol, polyglyceryl sorbitol, salts of pyrrolidonecarboxylic acid, potassium PCA, propylene glycol, saccharide isomerate, sodium glucuronate, sodium PCA, sorbitol, sucrose, trehalose, urea and xylitol.

Additional Ingredients

The compositions of the present disclosure can also include any one of, any combination of, or all of the following additional ingredients: water, a chelating agent, a UV absorption agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients. U.S. Pat. No. 9,814,670 (issued Nov. 14, 2017) describes many of these ingredients and is incorporated by reference in its entirety herein.

In some embodiments, the compositions of the disclosure contain water.

Chelating Agents

In some embodiments, the compositions of the disclosure contain chelating agents. Non-limiting examples of chelating agents include disodium ethylenediaminetetraacetic acid (EDTA) and tetrasodium EDTA.

UV Absorption Agents

In some embodiments, the compositions of the present disclosure include UV absorption agents. UV absorption agents include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis-diethylamino hydroxybenzoyl benzoate, bis benzoxazoylphenyl ethylhexylimino-triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl-4-methoxycinnamate. Non-limiting examples of physical sunblocks include, kaolin, talc, petrolatum and metal oxides (e.g., titanium dioxide and zinc oxide).

Emollients

In some embodiments, the compositions of the disclosure contain one or more emollients. Emollients are lubricating ingredients that make the skin soft and smooth and help the skin to retain moisture. Non-limiting examples of emollients include vegetable oils, mineral oils, shea butter, cocoa butter, petrolatum, cholesterol, silicone, and animal oils (including emu, mink, and lanolin).

Moisturizing Agent

In some embodiments, the compositions of the disclosure contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea *officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia *ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

In some embodiments, the compositions of the disclosure contain tocopherol. In some embodiments, the compositions of the disclosure contain tocopherol at a concentration between about 0% v/v and about 5% v/v. In some embodiments, the compositions of the disclosure contain tocopherol at a concentration between about 0.1% v/v and about 5% v/v. In some embodiments, the compositions of the disclosure contain tocopherol at about 0.01% v/v, about 0.02% v/v, about 0.03% v/v, about 0.04% v/v, about 0.05% v/v, about 0.06% v/v, about 0.07% v/v, about 0.08% v/v, about 0.09% v/v, about 0.10% v/v, about 0.15% v/v, about 0.20% v/v, about 0.25% v/v, about 0.3% v/v, about 0.35% v/v, about 0.4% v/v, about 0.45% v/v, about 0.50% v/v, about 0.55% v/v, about 0.60% v/v, about 0.65% v/v, about 0.70% v/v, about 0.75% v/v, about 0.80% v/v, about 0.85% v/v, about 0.90% v/v, about 0.95% v/v, about 1.0% v/v, about 2.0% v/v, about 3.0% v/v, about 4.0% v/v, or about 5.0% v/v, including all values and ranges in between.

Preservatives

In some embodiments, the compositions of the disclosure contain preservatives. Non-limiting examples of preservatives include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid and salts thereof, thimerosal, potassium sorbate, or combinations thereof. In some embodiments, paraben is not included in the formulations of the disclosure.

Thickening Agents

In some embodiments, the compositions of the disclosure contain thickening agents. Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture thereof.

Non-limiting examples of additional thickening agents that can be used in the context of the present invention include carboxylic acid polymers, cross-linked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., Carbopol™ 900 series from B. F. Goodrich).

Non-limiting examples of cross-linked polyacrylate polymers include cationic and nonionic polymers. Examples are described in U.S. Pat. Nos. 5,100,660; 4,849,484; 4,835,206; 4,628,078; 4,599,379, each of which is incorporated by reference in its entirety herein.

Non-limiting examples of polyacrylamide polymers (including nonionic polyacrylamide polymers including substituted branched or unbranched polymers) include polyacrylamide, iso-paraffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include *acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Silicone Containing Compounds

In some embodiments, the compositions of the disclosure contain a silicone containing compound. In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present disclosure include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present disclosure include those available from General Electric Co., Silicone Products Div., Waterford, N.Y. and SWS Silicones Div. of Stauffer Chemical Co., Adrian, Mich.

Essential Oils

In some embodiments, the compositions of the disclosure contain essential oils. Essential oils include oils derived from herbs, flowers, trees, and other plants. Such oils are typically present as tiny droplets between the plant's cells, and can be extracted by several method known to those of skill in the art (e.g., steam distilled, enfleurage (extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 g/mL to about 1.096 g/mL.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

Carrier Oils

In some embodiments, the compositions of the disclosure contain carrier oils. Carrier oils are used to dilute essential oils so they can be applied to the skin without side effects. Non-limiting examples of carrier oils include coconut oil (*Cocus nucifera*), black cumin seed oil (*Nigella sativa*), jojoba oil (*Simmondsia chinensis*), evening primrose oil (*Oenothera biennis*), rose hip oil (*Rosa mosqueta*), aloe (*Aloe vera*), and grapeseed oil (*Vitus vinifera*). In some embodiments, *Aloe vera* is used as a carrier oil.

Structuring Agents

In some embodiments, the compositions of the disclosure contain structuring agents. Structuring agents, in certain aspects, assist in providing rheological characteristics, which contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

Vitamins and Minerals

In some embodiments, the compositions of the disclosure contain one or more vitamins, minerals, or amino acids. Non-limiting examples of vitamins include vitamin A, ascorbic acid (vitamin C), vitamin D, vitamin E, vitamin K, thiamine, riboflavin, niacin, pantothenic acid, pyridoxine, biotin, folate, cobalamin, and cyanocobalamin. Non-limiting examples of minerals that can be included in the compositions of the present invention include antimony, barium, beryllium, bismuth, boron, bromine, calcium, carbon, cerium, cesium, chloride, chromium, cobalt, copper, dysprosium, erbium, europium, fluorine, gadolinium, gallium, germanium, gold, hafnium, holmium, indium, iodine, iridium, iron, lantharum, lithium, magnesium, manganese, molybdenum, neodymium, nickel, niobium, osmium, palladium phosphorus, platinum, potassium, paresodymium, rhenium, rhodium, rubidium, ruthenium, samarium, sodium, selenium, silicon, silver, sodium, strontium, sulfur, tantalum, thallium, thorium, tellurium, terbium, thulium, tin, titanium, tungsten, ytterbium, yttrium, zinc, and zirconium. Any soluble salt of these minerals suitable for inclusion edible products can be used, for example, calcium carbonate, calcium citrate, calcium malate, calcium-citrate-malate, calcium gluconate, magnesium citrate, magnesium gluconate, magnesium sulfate, zinc chloride, zinc sulfate, potassium iodide, and copper sulfate.

In some embodiments, the compositions of the disclosure include amino acids. Non-limiting examples of amino acids include alanine, glutamic acid, glycine, histidine, isoleucine, leucine, methionine, phenylalanine, serine, threonine, tryptophan, valine, aspartic acid, arginine, asparagine, glutamine, proline, cysteine, and lysine.

In some embodiments, the minerals and amino acids are contained within a product, which is incorporated into the compositions of the disclosure. For example, DERMA BOOST™ can be utilized in the compositions of the disclosure.

In some embodiments, the compositions of the disclosure contain retinoids. Retinoids have shown promise in the treatment of aging, burns, scaling, and dermatitis. Non-limiting examples of retinoids include retinol, tretinoin, adapalene, tazarotene, alitretinoin, isortetinoin, retinyl palmitate, retinaldehyde, and bexarotene.

Pharmaceutical Ingredients

In some embodiments, the compositions of the disclosure contain pharmaceutical ingredients. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including difluoromethylonithine (DFMO) and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, and wound healing agents.

In some embodiments, the pharmaceutical ingredient is a steroid. Non-limiting examples of steroids include dexamethasone, dexamethasone acetate, dexamethasone sodium phosphate, cortisone, cortisone acetate, hydrocortisone, hydrocortisone acetate, hydrocortisone cypionate, sodium hydrocortisone phosphate, prednisol hydrochloroneone acetate, prednisol acetate Prednisolone, Prednisolone Sodium Phosphate, Prednisolone Tebutate, Prednisolone Pivalate, Triamcinolone, Triamcinolone Acetonide, Triamcinolone Hexacetonide, Triamcinolone Diacetate, Methylprednisolone Methylprednisolone Acetate, Sodium Methodotassium Sodium Methionate, Sodium Methionate Diploate betamethasone, betamethasone, disodium phosphate of vetamethasone, sodium phosphate of vetamethasone, betamethasone acetate, disodium phosphate of betamethasone, chloroprednisone acetate, corticosterone, deoxycorticosterone, deoxycorticosterone acetate, deoxymethyrostaone deoxyketol ester, fludrocortisone, fludrocortisone acetate, dichlorisone acetate, fluorohydrocortisone, fluorometolone, fluprednisolone, parametasona, parametasona acetate, androsterone, fluoxymesterone, aldosterone, methandrostenolone, methyrostenedione, methyldostentaone testosterone, testosterone testosterone, testosterone equonates testosterone, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone hydroxyprogesterone, hydroxyprogesterone acetate, normethisterone, pregnenolone, progesterone, ethinyl estradiol, mestranol, dimethisterone, etisterone, ethinodiol diacetate, norethindrone, norethindrone acetate, norethisterone, fluocinolone acetonide, flurandrenolone, succinate hydrocortisone succinate, methylprednisolone sodium, prednisolone sodium phosphate, triamcinolone acetonide, sodium hydroxydione, spironolactone, oxandrolone, oxymetholone, prometholone, testosterone cypionate, testosterone phenylacetate, estradiol cypionate and noretynodrel.

Other Cosmetic Compositions

In some embodiments, the compositions of the disclosure contain other cosmetic compositions. In some embodiments, BEYOND FLAWLESS™ Second Skin is incorporated into the compositions or products of the disclosure. BEYOND FLAWLESS™ Second Skin contains graphene, stabilized vitamin C, peptides and extracts, which provide anti-aging skin care benefits.

In some embodiments, the compositions of the disclosure contain toners or texturizers.

In some embodiments, the cosmetics of the disclosure contain salicylic acid.

Antioxidants

In some embodiments, the compositions of the disclosure contain antioxidants. Antioxidants are substances that inhibit oxidation. Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, butated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Ingredients which May be Avoided

In some embodiments, one or more of the following ingredients is not included in the compositions of the disclosure. Non-limiting examples of ingredients that are not included are parabens, sulfates, alcohols, dyes, and fragrances. In some embodiments, the compositions of the disclosure do not include parabens. In some embodiments, the compositions of the disclosure do not include sulfates. In some embodiments, the compositions of the disclosure do not include alcohols. In some embodiments, the compositions of the disclosure do not include dyes. In some embodiments, the compositions of the disclosure do not include fragrances.

Cosmetic Vehicles

In some embodiments, the active ingredients and additional ingredients are mixed with a cosmetic vehicle. A cosmetic vehicle facilitates the delivery of an ingredient of the skin composition to the skin. In some embodiments, a cosmetic vehicle is selected from the group consisting of liposome, nanosome, emulsion, microemulsion, nanocapsules, solid lipid nanoparticles, and nanocrystals.

In some embodiments, the cosmetic vehicle is a liposome. Liposomes are vesicular structures, which have an aqueous core enclosed by a lipid bilayer. In some embodiments, liposomes contain phospholipids or fatty acids. In some embodiments, liposomes range in size from 15 nm in diameter to several micrometers in diameter. In some embodiments, liposomes exhibit a unilamellar structure or a multilamellar structure. Liposomes facilitate the continuous supply of active ingredients or additional ingredients to cells over a sustained period of time.

In some embodiments, the cosmetic vehicle is a nanosome. Nanosomes are liposomes with a particle size of between about 20 nm to about 600 nm. In some embodiments, the nanosomes of the disclosure have a particle size of about 20 nm, or about 30 nm, or about 40 nm, or about 50 nm, or about 60 nm, or about 70 nm, or about 80 nm, or about 90 nm, or about 100 nm, or about 200 nm, or about 300 nm, or about 400 nm, or about 500 nm, or about 600 nm. A representative methods for preparing liposomes is found in International Publication No. 2008/010241 (published Jan. 24, 2008), which is incorporated by reference herein, in its entirety. Example 1 shows a method of preparing liposomes.

In some embodiments, the cosmetic vehicle is an emulsion. An emulsion is a dispersed system containing at least two immiscible liquid phases, one of which is dispersed in the form of small droplets throughout the other, and an emulsifying agent to improve the stability of the system. Non-limiting examples of emulsifying agents include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

In some embodiments, emulsions are classified according to the droplet size of the liquids present in the emulsions. Nanoemulsions are systems containing droplets with particle sizes from 10 to 1000 nm. Microemulsions are systems containing droplets with particle sizes from about 5 nm to about 100 nm. McClements, which is incorporated by reference herein in its entirety, discusses characteristics of nanoemulsions and microemulsions (McClements. 2012, Soft Matter 8(6):1719-1729). Macroemulsions are systems containing droplets with average particle sizes between about 10 μm and about 1000 μm. In some embodiments, the emulsion is selected from the group consisting of water-in-oil, oil-in-water, silicone-in-water, and water-in-silicone. In some embodiments, the emulsion is a multiple emulsion system, such as water-in-oil-in-water, oil-in-water-in-oil, and oil-in-water-in-silicone. The name of the emulsion indicates the identities of the immiscible phases.

In some embodiments, "oil" signifies the oil phase of an emulsion. Non-limiting examples of oils which may be utilized within the oil phase include hydrocarbon oils of animal origin and hydrocarbon oils of vegetable origin. Non-limiting examples of hydrocarbon oils of vegetable origin include liquid triglycerides of fatty acids comprising 4 to 10 carbon atoms such as triglycerides of heptanoic or octanoic acids or also, for example, sunflower, corn, and soy, pumpkin, grape seeds, sesame, hazelnut, apricot, macadamia, arara, sunflower, castor, avocado, and triglycerides of caprylic/capric acids. In some embodiments, the oil phase of the emulsion contains from about 10% w/w to about 90% w/w. In some embodiments, the oil phase of the emulsion is about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, "water" signifies the water phase of an emulsion. In some embodiments, the water phase of the emulsion contains from about 10% w/w to about 90% w/w. In some embodiments, the water phase of the emulsion is about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, the cosmetic vehicle of the compositions of the disclosure is an oil-in-water emulsion. In some embodiments, the cosmetic vehicle comprises 55% w/w to 70% w/w water and further comprises glyceryl stearate, pentylene glycol, ethylhexyl isononanoate, cetyl alcohol, butyrosperum parkii (shea) butter, Zea mays (cor) germ oil, cetyl phosphate, cetearyl alcohol, and ceteareth-33. In some embodiments, the oil-in-water emulsion comprises 20% w/w to 40% w/w water and further comprises phospholipids, glycerin, and caprylic/capric triglycerides. In some embodiments, the oil-in-water emulsion comprises 3% v/v phospholipids, 54% v/v glycerin, and 10% v/v caprylic/capric triglycerides. An exemplary oil-in-water emulsion that may be used in the compositions of the disclosure is shown in Table 1.

TABLE 1

Exemplary oil-in-water emulsion

| Component | Weight percent (% v/v) |
| --- | --- |
| Phospholipids | 0-5 |
| Caprylic/capric triglyceride | 5-15 |
| Glycerin | 40-60 |

In some embodiments, the cosmetic vehicle is mixed with the other ingredients (i.e. active ingredients and additional ingredients) at a ratio of cosmetic vehicle to other ingredients of about 9:1 w/w, about 8:2 w/w, about 7:3 w/w, about 6:4 w/w, about 5:5 w/w, about 4:6 w/w, about 3:7 w/w, about 2:8 w/w, or about 1:9 w/w.

In some embodiments, the formulation containing rose oil, cannabidiol, a humectant, additional ingredients, and a cosmetic vehicle comprises about 3% w/w phospholipids (lecithin), about 54% w/w glycerin, about 10% w/w caprylic/capric triglyceride, about 1% w/w CBD, about 2% w/w rose oil, about 1% w/w humectant, about 0.1% w/w tocopherol, and water.

In some embodiments, the formulation containing rose oil, cannabidiol, a humectant, additional ingredients, and a cosmetic vehicle comprises about 3% w/w phospholipids (lecithin), about 54% w/w glycerin, about 10% w/w caprylic/capric triglyceride, about 1% w/w CBD, about 2% w/w rose oil, about 1% w/w humectant, and water.

In some embodiments, the formulation containing rose oil, cannabidiol, a humectant, additional ingredients, and a cosmetic vehicle comprises about 3% v/v phospholipids (lecithin), about 54% v/v glycerin, about 10% v/v caprylic/capric triglyceride, about 1% v/v CBD, about 2% v/v rose oil, about 1% v/v humectant, about 0.1% v/v tocopherol, and water.

In some embodiments, the formulation containing rose oil, cannabidiol, a humectant, additional ingredients, and a cosmetic vehicle comprises about 3% v/v phospholipids (lecithin), about 54% v/v glycerin, about 10% v/v caprylic/capric triglyceride, about 1% v/v CBD, about 2% v/v rose oil, about 1% v/v humectant, and water.

In some embodiments, the formulation containing rose oil, cannabidiol, a humectant, additional ingredients, and a cosmetic vehicle comprises about 3% v/v phospholipids (lecithin), about 54% v/v glycerin, about 10% v/v caprylic/capric triglyceride, about 1% w/v CBD, about 2% v/v rose oil, about 1% v/v humectant, about 0.1% v/v tocopherol, and water.

In some embodiments, the formulation containing rose oil, cannabidiol, a humectant, additional ingredients, and a cosmetic vehicle comprises about 3% v/v phospholipids (lecithin), about 54% v/v glycerin, about 10% v/v caprylic/capric triglyceride, about 1% w/v CBD, about 2% v/v rose oil, about 1% v/v humectant, and water.

In some embodiments, the formulation containing rose oil, cannabidiol, a humectant, additional ingredients, and a cosmetic vehicle comprises a formulation selected from any one of Formulations A-P, as described in Tables 2-5.

Properties and Stability of Formulation Containing Rose Oil, Cannabidiol, and Humectant In some embodiments, the compositions of the disclosure are stable for 12 or more months. In some embodiments, the compositions of the disclosure are stable for 12 months, or 13 months, or 14 months, or 15 months, or 16 months, or 17 months, or 18 months, or 19 months, or 20 months, or 21 months, or 22 months, or 23 months, or 24 months. In some embodiments, the compositions of the disclosure are stable for at least 12 months. In some embodiments, the compositions of the disclosure are stable at 25° C. in a closed container in a dark space.

In some embodiments, the compositions of the disclosure are liquids. In some embodiments, the compositions of the disclosure are green-yellowish.

In some embodiments, the compositions of the disclosure are stable from about pH 4.5 to about pH 7.5.

In some embodiments, the compositions of the disclosure have sensory features selected from the group consisting of light, hydrating, soothing, healing, and repairing.

In some embodiments, the compositions of the disclosure have physical features selected from the group consisting of smooth, silky, whipped cream, rich texture, easily spread onto the skin, and easily absorbed.

In some embodiments, the compositions of the disclosure have a pleasant smell.

Products Containing Rose Oil, Cannabidiol, and Humectant Formulation

In some embodiments, the compositions of the present disclosure is used in many cosmetic products. In some embodiments, the compositions of the present disclosure are incorporated into cosmetic products or alternative formulations at up to about 5% w/w. In some embodiments, the compositions are incorporated into cosmetic products or alternative formulations at about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.5% w/w, about 3.0% w/w, about 3.5% w/w, about 4.0% w/w, about 4.5% w/w, or about 5.0% w/w, including all values and ranges in between. In some embodiments, the compositions of the present disclosure are incorporated into cosmetic products or alternative formulations at between about 1% and about 2%.

Non-limiting examples of cosmetic products include, but are not limited to, lip sticks, lip balms, lip glosses, serums, face serums, sunscreen products, sunless skin tanning products, hair products, finger nail products, moisturizing creams, skin benefit creams and lotions, softeners, day lotions, gels, ointments, foundations, night creams, eye creams, face creams, cleansers, face masks, toners, masks, sheet masks, or other known cosmetic products or applications.

In some embodiments, the compositions of the present disclosure are incorporated into serums. Serums are skin care products that are designed to deliver high concentrations of active ingredients to the skin. In some embodiments, serums are clear, gel-based, or liquid. In some embodiments, serums are more hydrating than creams. In some embodiments, the compositions of the disclosure are incorporated into a water-based serum. In some embodiments, the compositions of the disclosure are incorporated into an oil-based serum. In some embodiments, serums are applied to the top of a face cream or lotion. In some embodiments, serums are applied directly to the skin. U.S. Publication No. 2004/0191330 (published Sep. 30, 2004) which describes how to apply a serum is incorporated by reference herein in its entirety.

In some embodiments, the compositions of the present disclosure are incorporated into a mask selected from the group consisting of sheet masks, clay masks, cream masks, peel-off masks, gel masks, charcoal masks, and sleep masks.

In some embodiments, the compositions of the disclosure are incorporated into charcoal masks or clay masks. In some embodiments, charcoal masks and clay masks draw out impurities form a person's skin. In some embodiments, charcoal masks and clay masks are used to brighten the skin.

In some embodiments, the compositions of the disclosure are incorporated into gel masks, which have a cooling sensation. In some embodiments, cream masks are applied to dry skin. In some embodiments, clay and charcoal masks are applied to oily skin.

In some embodiments, the compositions of the present disclosure are incorporated in sheet masks. In some embodiments, a sheet mask contains a fabric soaked in a serum containing the composition of the disclosure. Non-limiting examples of fabrics used for sheet masks include cotton, microfiber, cupra, tencel, hydrogels, bio-cellulose, foil, and charcoal. In some embodiments, a sheet mask is applied to skin. In some embodiments, the sheet mask is applied to a person's face. In some embodiments, a sheet mask is applied to a person's eyes, nose, lips, décolletage, hair, or feet.

In some embodiments, a mask containing the compositions of the present disclosure is washed off with water. In some embodiments, a peel-off mask containing the compositions of the present disclosure is peeled off.

In some embodiments, the compositions of the present disclosure are incorporated into eye creams. In some embodiments, eye creams are applied to the delicate skin around the eye. In some embodiments, eye creams are applied around the eyes to reduce puffiness and dark circles. In some embodiments, eye creams are applied to moisturize the area of skin around the eyes. In some embodiments, eye creams are applied to firm the skin around the eyes. In some embodiments, application of eye creams around the eyes decreases fine lines and wrinkles. U.S. Publication No. 2004/0191330 (published Sep. 30, 2004) which describes how to apply an eye cream is incorporated by reference herein in its entirety.

In some embodiments, the compositions of the present disclosure are incorporated into face creams. In some embodiments, face creams are applied to a person's face. In some embodiments, face creams are used to moisturize a person's face. In some embodiments, face creams are applied at night. In some embodiments, face creams are applied in the morning.

In certain embodiments, products containing rose oil, cannabidiol, and humectants are placed in a container. The container can be a bottle, dispenser, or package. The container can dispense a pre-determined amount of the composition. In certain aspects, the composition is dispensed in a spray, mist, dollop, or liquid. In some embodiments, the composition is placed in a 15 ml glass canister. In some embodiments, the composition is placed in a 30 mL glass canister. The container can include indicia on its surface. The indicia can be a word, an abbreviation, a picture, or a symbol.

Methods of Using the Compositions of the Disclosure

In some embodiments, the compositions of the disclosure are used for regulating a skin condition. In some embodiments, the compositions are applied topically to a subject's skin. In some embodiments, the subject is a mammal. In some embodiments, the subject is an animal or a human. Non-limiting examples of animals include dogs, cats, wolves, bears, tigers, lions, monkeys, guinea pigs, ferrets, pigs, hamsters, and rabbits.

In some embodiments, the compositions are applied to the skin. In some embodiments, the compositions of the disclosure are applied to the epidermis. In some embodiments, the compositions of the disclosure penetrate the dermis. In some embodiments, the compositions of the disclosure penetrate the hypodermis. In some embodiments, the compositions of the disclosure are applied to the face, scalp, hands, neck, décolleté, scalp, paw, hand, palm, arm, leg, foot, sole, chest, breast, back, abdomen, buttock, vulva, eyelid, nipples, penis, scrotum, anus, or any other skin areas of a subject. In some embodiments, the compositions of the disclosure are applied to the lips. In some embodiments, the composition is applied to the whole body.

In some embodiments, the compositions of the disclosure are applied to the hair. The compositions may serve as a shampoo, conditioner, detangler, or a leave-in conditioner.

In some embodiments, the compositions are applied as a product of the disclosure, described above. In some embodiments, the compositions are applied for an extended period for an aesthetic, prophylactic, or therapeutic benefit (i.e. a "leave-on" composition). In some embodiments, the leave-on composition is left on the skin for a period of at least 1 minute, or at least 2 minutes, or at least 3 minutes, or at least 4 minutes, or at least 5 minutes, or at least 6 minutes, or at least 7 minutes, or at least 8 minutes, or at least 9 minutes, or at least 10 minutes, or at least 15 minutes, or at least 20 minutes, or at least 25 minutes, or at least 30 minutes, or at least 45 minutes, or at least 1 hour, or at least 12 hours, or up to 24 hours, including all ranges in between.

In some embodiments, the compositions are applied one or more times per day. In some embodiments, the compositions are applied once per day. In some embodiments, the compositions are applied twice a day, or three times a day, or four time a day, or more. In some embodiments, the compositions are applied every other day, or every third day, or every fourth day, or every fifth day, or every sixth day, or once per week.

In some embodiments, the compositions of the disclosure are used to regulate a skin condition. In some embodiments, the compositions are used to regulate visible, tactile, or visible and tactile discontinuities in the skin. In some embodiments, the discontinuities are associated with aging. In some embodiments, the discontinuities are associated with puberty. Non-limiting examples of discontinuities include acne, fine lines, wrinkles, dark spots, burns, stretch marks, and enlarged pores. In some embodiments, the compositions of the disclosure are used to treat psoriasis, dermatitis, sunburn, and rosacea. In some embodiments, the compositions of the disclosure are have properties selected from the group consisting of anti-bacterial, anti-inflammatory, and anti-oxidants. In some embodiments, the compositions of the disclosure are anti-inflammatory. In some embodiments, the compositions of the disclosure are anti-oxidants. In some embodiments, the compositions of the disclosure are anti-bacterial.

In some embodiments, the compositions of the disclosure are applied for hydration of the skin. In some embodiments, the compositions of the disclosure are used as a sunblock. In some embodiments, the compositions of the disclosure are utilized to prevent photo-aging. In some embodiments, the compositions of the disclosure are utilized to repair skin cells. In some embodiments, the compositions of the disclosure are used to protect skin from external factors. In some embodiments, the compositions of the disclosure are used for eye care. In some embodiments, the compositions of the disclosure are used to reduce fine lines or wrinkles near the eyes.

In some embodiments, when a subject is treated with the compositions of the disclosure, the subject exhibits a reduction in acne compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, when a subject is treated with the compositions of the disclosure, the subject exhibits a reduction in fine lines compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, when a subject is treated with the compositions of the disclosure, the subject exhibits a reduction in wrinkles compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, when a subject is treated with the compositions of the disclosure, the subject exhibits a reduction in dark spots compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, when a subject is treated with the compositions of the disclosure, the subject exhibits a reduction in stretch marks compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, when a subject with a wound is treated with the compositions of the disclosure, the subject exhibits healing of the wound. In some embodiments, the compositions of the disclosure cause migration of skin cells or skin stem cells to the wound.

In some embodiments, the compositions of the disclosure are anti-inflammatory. In some embodiments, the compositions of the disclosure inhibit $PGE_2$ release by keratinocytes. In some embodiments, the compositions of the disclosure reduce secretion of an inflammatory marker. In some embodiments, the disclosure inhibit release of one or more chemokines, including but not limited to IL-8. In some embodiments, the disclosure inhibit or augment release of one or more cytokines.

In some embodiments, regulation of skin condition can be visualized, analyzed, measured and quantified using many techniques known by the specialist in cosmetic or skin rejuvenation treatments.

In some embodiments, decrease of fine lines, wrinkles, skin folds, and of skin roughness can be quantified either directly on the person contact-free using fringe projection (FOITS=Fast Optical In vivo Topometry System; Dermatop™ or Primos™ system), or by silicon replicas of the skin area which are then analyzed by the technique called "drop shadows" or by a FOITS system, or by a Canfield VISIA™ device. Changes in volume and shape of the face can be quantified using a relief obtaining system without contact using a fringe projection FOITS system. Alteration of the skin barrier can be quantified by measuring transepidermal water loss (TEWL) using a Tewameter™, a Vapometer™, a Dermalab™, and/or an Aquaflux™ device. Loss of firmness and/or elasticity and/or tone and fatigue of the skin can be quantified using a Cutometer™, a Reviscometer™, an Aeroflexmeter™, a Dynaskin™, a Ballistometer™, a Twistometer™ and/or a Dermalab™ device. Dull complexion, loss of uniformity of skin tone, pigmentation changes (hypo and hyper pigmentation), local reddening, loss of clarity and brightness of the complexion, pigmentation spots, rosacea, dark circles are directly measurable using a Mexameter™, a Chromameter™, a Colormeter™, a Canfield VISIA™, a Canfield VISIA-CR™, a SIAscope™, a Goniolux™ or a confocal laser microscope device, and/or by specific color analysis on photo (enabled by the technique of photographing in polarized crossed and parallel light). The number and size of facial pores can be quantified by the silicon replica technology described above, or by specific analysis on photo (enabled by using a video microscope or a macroscopic photographing system). Atrophy and thinning of the skin, epidermis, dermis, or hypodermis (e.g., in case of studying slimming agents) is measurable by measuring TEWL (e.g., in case of studying the epidermis), or by an ultrasound echographic device, and/or a confocal laser microscope device. Density of skin fibers can be quantified by ultrasound and then by image analysis. Cellulite is quantified either directly by a relief obtaining system without contact using fringe projection (FOITS) or indirectly by measuring the length of the dermo-hypodermal junction by an ultrasound echographic device. Stretch marks are either directly quantified using a relief obtaining system without contact using fringe projection (FOITS) or by the silicon replica technology. Skin softness is directly measurable by techniques of friction study as with a frictiometer device or indirectly by the silicon replica technology. Changes in collagen, extracellular matrix components, and/or in connective tissue fibers may be quantified by histology, confocal laser microscopy, UV spectroscopy, SIAscopie, and/or by multiphoton spectroscopy. All changes visible to the eye (including but not limited to fine lines, wrinkles, folds, texture, sagging, loss of elasticity color, tone, pigmentation, redness) can be quantified in direct or on photography, by a trained judge person or not, with or without visual scoring system (e.g., using a 4-point severity scale).

EXAMPLES

Example 1. Preparation of Nanosomes Containing Rose Oil in the Form of an Extract of *Rhododendron ferrugineum* (e.g. AlpineRoseActive™), Cannabidiol, and Glycoin Nanosomes containing rose oil, cannabidiol, and a humectant were prepared.

Nanosomes were prepared by mixing phospholipids, glycerin, and caprylic/capric triglycerides. The resultant solution was homogenized with a microfluidizer at 1200 bar. The particle size of the liposomes was analyzed using a photon correlation spectrometer. The average particle size of the liposomes was 90±50 nm.

The nanosomes were mixed at a 1:1 w/w ratio with an extract from *Rhododendron ferrugineum*, CBD, and glyceryl glucoside to form nanosomes encompassing the stem cell extract, CBD, and glyceryl glucoside. Table 2 shows the concentrations of the components in the resultant compositions.

TABLE 2

Exemplary Composition containing *Rhododendron ferrugineum*, CBD, and glycoin

| Component | Formulation A | Formulation B | Formulation C | Formulation D |
|---|---|---|---|---|
| Phospholipids | 3% v/v | 3% v/v | 3% v/v | 3% v/v |
| Glycerin | 54% v/v | 54% v/v | 54% v/v | 54% v/v |
| Caprylic/capric triglyceride | 10% v/v | 10% v/v | 10% v/v | 10% v/v |
| cannabidiol | 1% w/v | 1% w/v | 1% v/v | 1% v/v |
| extract from *Rhododendron ferrugineum* | 2% v/v | 2% v/v | 2% v/v | 2% v/v |
| Glyceryl glucoside | 1% v/v | 1% v/v | 1% v/v | 1% v/v |
| tocopherol | 0.1% v/v | | 0.1% v/v | |

Example 2. Preparation of Nanosomes Containing Rose Oil in the Form of an Extract of *Rosa gallica* Linne (e.g. Rose Absolute Egyptian Rose), Cannabidiol, and Glycoin Nanosomes containing rose oil, cannabidiol, and a humectant were prepared.

Nanosomes were prepared by mixing phospholipids, glycerin, and caprylic/capric triglycerides. The resultant solution was homogenized with a microfluidizer at 1200 bar. The particle size of the liposomes was analyzed using a photon correlation spectrometer. The average particle size of the liposomes was 90±50 nm.

The nanosomes were mixed at a 1:1 w/w ratio with an extract from *Rosa gallica* Linne, CBD, and glyceryl glucoside to form nanosomes encompassing the stem cell extract, CBD, and glyceryl glucoside. Table 3 shows the concentrations of the components in the resultant composition.

TABLE 3

Exemplary Composition containing *Rosa gallica Linne* extract, CBD, and glycoin

| Component | Formulation E | Formulation F | Formulation G | Formulation H |
|---|---|---|---|---|
| Phospholipids | 3% v/v | 3% v/v | 3% v/v | 3% v/v |
| Glycerin | 54% v/v | 54% v/v | 54% v/v | 54% v/v |
| Caprylic/capric triglyceride | 10% v/v | 10% v/v | 10% v/v | 10% v/v |
| cannabidiol | 1% w/v | 1% w/v | 1% v/v | 1% v/v |
| extract from *Rosa gallica Linne* | 2% v/v | 2% v/v | 2% v/v | 2% v/v |
| Glyceryl glucoside | 1% v/v | 1% v/v | 1% v/v | 1% v/v |
| tocopherol | 0.1% v/v | | 0.1% v/v | |

Example 3. Preparation of Nanosomes Containing Rose Oil in the Form of an Extract of *Rhododendron ferrugineum* (e.g. AlpineRoseActive™), Cannabidiol, and Hyaluronic Acid Nanosomes containing rose oil, cannabidiol, and a humectant were prepared.

Nanosomes were prepared by mixing phospholipids, glycerin, and caprylic/capric triglycerides. The resultant solution was homogenized with a microfluidizer at 1200 bar. The particle size of the liposomes was analyzed using a photon correlation spectrometer. The average particle size of the liposomes was 90±50 nm.

The nanosomes were mixed at a 1:1 w/w ratio with an extract from *Rhododendron ferrugineum*, CBD, and hyaluronic acid to form nanosomes encompassing the stem cell extract, CBD, and hyaluronic acid. Table 4 shows the concentrations of the components in the resultant composition.

TABLE 4

Exemplary Compositions containing *Rhododendron ferrugineum*, CBD, and hyaluronic acid

| Component | Formulation I | Formulation J | Formulation K | Formulation L |
|---|---|---|---|---|
| Phospholipids | 3% v/v | 3% v/v | 3% v/v | 3% v/v |
| Glycerin | 54% v/v | 54% v/v | 54% v/v | 54% v/v |
| Caprylic/capric triglyceride | 10% v/v | 10% v/v | 10% v/v | 10% v/v |
| cannabidiol | 1% w/v | 1% w/v | 1% v/v | 1% v/v |
| extract from *Rhododendron ferrugineum* | 2% v/v | 2% v/v | 2% v/v | 2% v/v |
| hyaluronic acid | 1% v/v | 1% v/v | 1% v/v | 1% v/v |
| tocopherol | 0.1% v/v | | 0.1% v/v | |

Example 4. Preparation of Nanosomes Containing Rose Oil in the Form of an Extract of *Rosa gallica* Linne (e.g. Rose Absolute Egyptian Rose), Cannabidiol, and Hyaluronic Acid Nanosomes containing rose oil, cannabidiol, and a humectant were prepared.

Nanosomes were prepared by mixing phospholipids, glycerin, and caprylic/capric triglycerides. The resultant solution was homogenized with a microfluidizer at 1200 bar. The particle size of the liposomes was analyzed using a photon correlation spectrometer. The average particle size of the liposomes was 90±50 nm.

The nanosomes were mixed at a 1:1 w/w ratio with an extract from *Rosa gallica* Linne, CBD, and hyaluronic acid to form nanosomes encompassing the stem cell extract, CBD, and hyaluronic acid. Table 5 shows the concentrations of the components in the resultant compositions.

TABLE 5

Exemplary Compositions containing *Rosa gallica* Linne extract, CBD, and glycoin

| Component | Formulation M | Formulation N | Formulation O | Formulation P |
|---|---|---|---|---|
| Phospholipids | 3% v/v | 3% v/v | 3% v/v | 3% v/v |
| Glycerin | 54% v/v | 54% v/v | 54% v/v | 54% v/v |
| Caprylic/capric triglyceride | 10% v/v | 10% v/v | 10% v/v | 10% v/v |
| cannabidiol | 1% w/v | 1% w/v | 1% v/v | 1% v/v |
| extract from *Rosa gallica* Linne | 2% v/v | 2% v/v | 2% v/v | 2% v/v |
| hyaluronic acid | 1% v/v | 1% v/v | 1% v/v | 1% v/v |
| tocopherol | 0.1% v/v | | 0.1% v/v | |

Example 5. Method of Treating Acne

The ability of the nanosomes of Examples 1-4 to treat acne will be measured. As negative controls, nanosomes which lack one or more of the active ingredients will be utilized (e.g. nanosomes which contain rose oil and a humectant but not CBD, nanosomes which contain a humectant and CBD but not rose oil). The nanosomes will be incorporated into a lotion and applied to a subject with acne's face. Photographs before treatment and every day after treatment will be used to determine the efficacy of the nanosomes for treating acne.

Example 6. Method of Reducing Wrinkles

The ability of the nanosomes of Examples 1-4 to reduce wrinkles will be measured. As negative controls, nanosomes which lack one or more of the active ingredients (e.g. nanosomes which contain rose oil and a humectant but not CBD, nanosomes which contain a humectant and CBD but not rose oil) will be utilized. The nanosomes will be incorporated into a lotion and applied to a subject with wrinkle's face. Photographs before treatment and every day after treatment will be used to determine the efficacy of the nanosomes for reducing wrinkles.

Example 7. Cytotoxicity of Composition Containing Rose Oil, a Humectant, and CBD The cytotoxicity of S-863d and S-863g on normal human epidermal keratinocytes (NHEK) was evaluated.

Materials: NHEK cells were used at the third passage and cultured at 37° C. in the presence of 5% $CO_2$. The NHEK cells were grown in keratinocyte serum free media supplemented with gentamycin (25 µg/mL). S-863d contained 3% v/v phospholipids, 54% v/v glycerin, 10% v/v caprylic/capric triglyceride, 1% w/v cannabidiol, 2% v/v AlpineRoseActive™, 1% v/v glycoin, 0.1% v/v tocopherol, and water (ad 100%). The particle size (zAve) of S-863d was 90±50 nm, and the pH of S-863d was between 4.5 and 7.5. The total germ count of S-863d was <100 CFU/g. S-863d was stored at 4° C. in a dark space in a closed container. S-863g (negative control) contained 1% CBD in DMSO. S-863d was evaluated at 0.004%, 0.02%, and 0.1%. S-863g was evaluated at 0.00044%, 0.0013%, and 0.004%.

Methods: A MTT reduction assay was performed to evaluate the cytotoxicity of S-863d and S-863g on NHEK cells. NHEK cells were treated with S-863d or S-863g and incubated for 48 hours. After 48 hours, the NHEK cells were incubated with MTT (tetrazolium salt) reduced in blue formazan crystals by succinate dehydrogenase (mitochondrial enzyme). The transformation was proportional to enzyme activity. After cell dissociation and formazan crystal solubilization using DMSO, the optical density (OD) of the extracts at 40 nm was recorded. The OD was measured with a spectrometer (VERSAmax, Molecular Devices) and was used to estimate the proportion of living cells and their metabolic activity.

Viability was measured according to the following formula: viability (%)=($OD_{sample}/OD_{control}$)×100.

The effect of S-863d and S-863g on cytotoxicity are found in Tables 6 and Table 7.

TABLE 6

Effect of compound S-863d on the viability of keratinocytes after 48 hours of incubation

|  | Control | | S-863d Unit: % | | | | | | | |
|---|---|---|---|---|---|---|---|---|---|---|
|  |  |  | 1.83E−04 | 0.001 | 0.003 | 0.012 | 0.047 | 0.188 | 0.750 | 3 |
| Viability | 96 | 88 | 94 | 89 | 83 | 81 | 94 | 93 | 51 | 38 |
|  | 107 | 105 | 97 | 91 | 82 | 87 | 101 | 100 | 58 | 47 |
|  | 102 | 102 | 101 | 102 | 88 | 90 | 100 | 98 | 58 | 49 |
| Mean | 100 | | 97 | 94 | 85 | 86 | 98 | 97 | 56 | 45 |
| Sem | 3 | | 2 | 4 | 2 | 3 | 2 | 2 | 2 | 3 |
| Morphological Observations |  |  | + | + | + | + | +/− | +/−, * | −, * | −, op |

Codification
+: normal population;
+/−: growth reduction;
−: toxicity;
0: cell mortality
g: grains of compound;
op: opacity of the compound;
* morphological modification;
ag: agglutinated cells

TABLE 7

Effect of compound S-863 g on the viability of keratinocytes after 48 hours of incubation

|  | Control | | S-863 g Unit: % | | | | | | | |
|---|---|---|---|---|---|---|---|---|---|---|
|  |  |  | 1.83E−04 | 0.001 | 0.003 | 0.012 | 0.047 | 0.188 | 0.750 | 3 |
| Viability | 102 | 94 | 100 | 102 | 100 | 0 | 1 | 0 | 5 | 17 |
|  | 103 | 99 | 105 | 108 | 97 | 0 | 1 | 0 | 8 | 26 |
|  | 105 | 97 | 106 | 104 | 101 | 1 | 1 | 0 | 8 | 24 |
| Mean | 100 | | 104 | 105 | 99 | 0 | 1 | 0 | 7 | 23 |
| Sem | 2 | | 2 | 2 | 1 | 0 | 0 | 0 | 1 | 3 |
| Morphological Observations |  |  | + | + | + | −, * | −, * | −, *, g | 0, g | op |

Codification
+: normal population;
+/−: growth reduction;
−: toxicity;
0: cell mortality
g: grains of compound;
op: opacity of the compound;
* morphological modification;
ag: agglutinated cells Example 8. Effect of Composition Containing Rose Oil, a Humectant, and CBD on Migration of Human Keratinocyte Stem Cells The effect of S-863d and S-863g on wound healing in keratinocytes was evaluated. The migration of human keratinocyte stem cells (KSC) was evaluated by measuring wound recovery using imaging on a system whereby a "wound gap" was created by scratching.

Materials: Human keratinocyte cells (KSC) were used at the third passage and cultured at 37° C. in the presence of 5% CO2. The NHEK cells were grown in keratinocyte serum free media supplemented with gentamycin (25 µg/mL), pituitary extract (PE) (25 µg/mL), and epidermal growth factor (EGF) (0.25 ng/ml). S-863d contained 3% phospholipids, 54% glycerin, 10% caprylic/capric triglyceride, 1% cannabidiol, 2% AlpineRoseActive™, 1% glycoin, 0.1% tocopherol, and water (ad 100%). The particle size (zAve) of S-863d was 90±50 nm, and the pH of S-863d was between 4.5 and 7.5. The total germ count of S-863d was <100 CFU/g. S-863d was stored at 4° C. in a dark space in a closed container. S-863g (negative control) contained 1% CBD in DMSO. S-863d was evaluated at 0.004%, 0.02%, and 0.1%. S-863g was evaluated at 0.00044%, 0.0013%, and 0.004%.

Methods: The KSCs were seeded in 24-well plates (previously coated with a collagen I solution) and cultured in culture medium for 24 hours. The medium was then replaced by assay medium and an artificial "wound gap" was generated by scratching the cell monolayers. The KSCs were labeled with calcein-AM. After 30 minutes of incubation (TO), the medium was replaced by assay medium containing or not (control condition) the test compounds or the reference compound (e.g. epidermal growth factor (EGF) at 10 ng/mL) and the cells were further incubated for 24 hours. The labeling with calcein-AM was renewed before the final timepoint. All experimental conditions were performed in triplicate. Cell migration into the migration zone was observed after 0 (TO) and 24 hours of incubation using a high-resolution imaging system INCell Analyzer™ 2200 (GE Healthcare) automated microscope and the artificial wound area was analyzed using ImageJ software. One picture was taken per well (objective lens ×4). The artificial wound area was measured after 24 hours of incubation and compared to the area measured at TO in order to visualize and quantify the wound recovery. The effect of compounds on cell migration was compared to the untreated control.

The migration area (percentage of wound recovery) was calculated using the following formula:

$$\text{Wound recovery (\%)} = 100 - \left(\frac{\text{Wound Area}}{\text{Initial Wound Area}} \times 100\right).$$

In the control condition, KSC migration was moderate with a mean wound recovery of 40% after 24 hours of incubation. The reference compound, EGF, induced a marked stimulation on KSC migration. Indeed, the wound gap recovery reached 73% after 24 hours of incubation, validating the assay. Compound S-863d, tested at 0.004%, 0.02%, and 0.1%, stimulated the migration of keratinocytes and reached a maximum of about 201% of the control at a concentration of 0.02%.

Compound S-863g, tested at 0.00044% and 0.0013%, also stimulated wound recovery at a slightly lower level than S-863d (maximum 176% of the control—although the tested concentrations were lower). Table 10 shows the effect of compounds S-863d and S-863g on the migration of KSCS after 24 hours of incubation. The underlined images from Table 8 are shown in FIG. 1. FIG. 1 shows representative images of the effect of compounds S-863d and S-863g on the migration of KSCs.

Example 9. Effect of Composition Containing Rose Oil, a Humectant, and CBD on IL-8 and Prostaglandin E2 Release by a Keratinocyte Cell Line The effect of S-863d and S-863g on inflammation in keratinocytes was evaluated by measuring phorbol myristate acetate (PMA)-induced interleukin-8 (IL-8) and prostaglandin E2 ($PGE_2$) release from a NCTC-2544 keratinocyte cell line by enzyme-linked immunosorbent assay (ELISA).

Materials: A NCTC-2544 human keratinocyte cell line (NCTC-2544 cells) was cultured at 37° C. in the presence of 5% CO2. The NCTC-2544 cells were grown in Dulbecco's Modified Eagle Medium (DMEM) supplemented with L-glutamine (2 mM), penicillin (50 U/mL), Streptomycin (50 µg/mL), and fetal calf serum (FCS) (10%). S-863d contained 3% phospholipids, 54% glycerin, 10% caprylic/capric triglyceride, 1% cannabidiol, 2% AlpineRoseActive™, 1% glycoin, 0.1% tocopherol, and water (ad 100%). The particle size (zAve) of S-863d was 90±50 nm, and the pH of S-863d was between 4.5 and 7.5. The total germ count of S-863d was <100 CFU/g. S-863d was stored at 4° C. in a dark space in a closed container. S-863g (negative control) contained 1% CBD in DMSO. S-863d was evaluated at 0.004%, 0.02%, and 0.1%. S-863g was evaluated at 0.00044%, 0.0013%, and 0.004%.

Methods: The keratinocytes were seeded in 96-well plates and cultured for 24 hours in culture medium. The medium was then replaced by culture medium containing or not (control) the test compounds or the reference compound (dexamethasone at $10^{-7}$ M for IL-8 assay and indomethacin at $10^{-6}$ M for $PGE_2$ assay) and the cells were pre-incubated for 24 hours. After pre-incubation, the medium was replaced

TABLE 8

Effect of compounds S-863 d and S-863 g on the migration of keratinocyte stem cells after 24 hours of incubation

| | | | T0 | 24 Hours | | | | | | |
|---|---|---|---|---|---|---|---|---|---|---|
| Treatment | | | Initial Wound Area | Wound area | Wound Recovery | Mean | Sem | % | sem | |
| Test compound | Concentration | Image | (mm²) | (mm²) | (%) | (%) | (%²) | Control | (%) | p[(1)] |
| Control | — | T-1 | 2.56 | 1.51 | 41 | 40 | 1 | 100 | 3 | — |
| | | T-2 | 2.26 | 1.32 | 42 | | | | | |
| | | T-3 | 2.39 | 1.49 | 37 | | | | | |
| EGF | 10 ng/ml | R-1 | 2.35 | 0.46 | 80 | 73 | 5 | 183 | 12 | ** |
| | | R-2 | 1.99 | 0.50 | 75 | | | | | |
| | | R-3 | 2.11 | 0.76 | 64 | | | | | |
| S-863 d | 0.004% | 43-1 | 2.35 | 0.75 | 68 | 63 | 3 | 157 | 8 | ** |
| | | 43-2 | 1.75 | 0.75 | 57 | | | | | |
| | | 43-3 | 1.88 | 0.70 | 63 | | | | | |
| | 0.02% | 42-1 | 2.48 | 0.58 | 77 | 80 | 3 | 201 | 9 | *** |
| | | 42-2 | 1.85 | 0.42 | 77 | | | | | |
| | | 42-3 | 2.45 | 0.31 | 87 | | | | | |
| | 0.1% | 41-1 | 2.41 | 0.71 | 71 | 80 | 5 | 200 | 12 | ** |
| | | 41-2 | 2.23 | 0.27 | 88 | | | | | |
| | | 41-3 | 1.88 | 0.35 | 81 | | | | | |
| S-863 g | 0.00044% | 73-1 | 1.72 | 0.77 | 55 | 66 | 8 | 164 | 21 | * |
| | | 73-2 | 1.43 | 0.25 | 82 | | | | | |
| | | 73-3 | 2.28 | 0.92 | 60 | | | | | |
| | 0.0013% | 72-1 | 1.93 | 0.17 | 91 | 71 | 11 | 176 | 26 | * |
| | | 72-2 | 1.87 | 0.71 | 62 | | | | | |
| | | 72-3 | 2.51 | 1.04 | 58 | | | | | |
| | 0.004% | 71-1 | 2.30 | 1.16 | 49 | 50 | 5 | 124 | 12 | ns |
| | | 71-2 | 1.79 | 1.05 | 41 | | | | | |
| | | 71-3 | 2.17 | 0.90 | 58 | | | | | |

[(1)]Threshold for statistical significance;
ns: >0.05 Not significant;
* 0.01 to 0.05 Significant;
** 0.001 to 0.01 Very significant;
*** <0.001, Extremely significant by culture medium containing or not (control) the test compounds or the reference compounds and the inflammatory inducer phorbol myristate acetate (PMA) at 0.1 µg/mL was added. The cells were further incubated for 24 hours. A control without inducer was performed in parallel (non-stimulated control condition). All experimental conditions were performed in triplicate. IL-8 and PGE2 released in the culture supernatants were measured by ELISA.

Inhibition of IL-8 and PMA-induced $PGE_2$ release was measured using the following formula:

$$\text{Relative Inhibition (\%)} = \left(\frac{Mean_{stimulated\ control} - \text{Value}}{Mean_{stimulated\ control} - Mean_{non\text{-}stimulated\ control}}\right) \times 100.$$

Results: A treatment of NCTC-2544 keratinocytes with PMA at 0.1 µg/mL strongly increased IL-8 release (~120000 pg/mL) while basal IL-8 release was limited in the non-stimulated control condition (~350 pg/mL). The reference compound, dexamethasone, tested at $10^{-7}$ M, strongly inhibited PMA-induced IL-8 release (18% of the stimulated control), validating the assay. Under the experimental conditions of the assay, compounds S-863d and S-863g did not have any significant effect on PMA-induced IL-8 release in the NCTC-2544 cells, as shown in Table 9.

Under non-stimulated control conditions, no basal $PGE_2$ release was detected in NCTC-2544 keratinocytes and the treatment with PMA at 0.1 µg/mL resulted in a very strong release of $PGE_2$ (~220000 pg/mL). The reference compound indomethacin, tested at $10^{-6}$M, completely inhibited this effect, validating the assay. Under the experimental conditions of this study, compound S-863d presented a trend for a concentration-dependent inhibitory effect on PMA-induced PGE2 release, reaching 59% of the control when tested at 0.1%. Compound S-863g did not display any clear effect on PMA-induced PGE2 release in the NCTC-2544 cells. Table 10 shows the results of this study.

The results of this study showed that compound S-863d exhibited anti-inflammatory properties by inhibiting $PGE_2$ release by keratinocytes stimulated with PMA. This formulation also had a strong stimulating effect on keratinocyte migration suggesting that it has interesting wound healing properties. In contrast, S-863g, tested as a negative control, had no anti-inflammatory properties and its stimulating effect on keratinocyte migration was less marked than compound S-863d.

TABLE 9

Effect of compounds S-863 d and S-863 g on PMA-induced IL-8 release by NCTC-2544 keratinocytes

| Treatment | | | Basic data | | | | | Normalized data | | |
|---|---|---|---|---|---|---|---|---|---|---|
| Test compound | Concentration | IL-8 (pg/ml) dilution factor adjusted | Mean (pg/ml) | sem (pg/ml) | % Stimulated control | sem (%) | $p^{(1)}$ | % Relative inhibition | sem (%) | $p^{(1)}$ |
| Non-stimulated control[#] | — | 363 336 347 | 349 | 8 | 0 | 0 | *** | 100 | 0 | *** |
| Stimulated conditions: PMA - 0.1 µg/ml   Control | — | 109321 115910 135021 | 120084 | 7707 | 100 | 6 | — | 0 | 6 | — |
|   Dexamethasone | $10^{-7}$ M | 18117 23002 25217 | 22112 | 2097 | 18 | 2 | *** | 82 | 2 | *** |
|   S-863 d | 0.004% | 116481 158416 166618 | 147172 | 15527 | 123 | 13 | ns | −23 | 13 | ns |
| | 0.02% | 116531 159116 126429 | 134025 | 12866 | 112 | 11 | ns | −12 | 11 | ns |
| | 0.1% | 132589 142324 185512[(2)] | 137457 | 4867 | 114 | 4 | nc | −15 | 4 | nc |
|   S-863g | 0.00044% | 92046 107904 107401 | 102451 | 5204 | 85 | 4 | ns | 15 | 4 | ns |
| | 0.0013% | 93461 113257 94796 | 100505 | 6388 | 84 | 5 | ns | 16 | 5 | ns |
| | 0.004% | 102302 116902 96167 | 105124 | 6150 | 88 | 5 | ns | 12 | 5 | ns |

[(1)]Threshold for statistical significance
ns: >0.05, Not significant
\* 0.01 to 0.05, Significant
\*\* 0.001 to 0.01, Very significant
\*\*\* <0.001, Extremely significant
nc: Not calculable
[(2)]Rejected Data
[#]Non-diluted samples

TABLE 10

Effect of compounds S-863 d and S-863 g on PMA-induced PGE$_2$ release by NCTC-2544 keratinocytes

| Treatment | | Basic data | | | | | | Normalized data | | |
|---|---|---|---|---|---|---|---|---|---|---|
| | | PGE$_2$ (pg/ml) dilution factor adjusted | Mean (pg/ml) | sem (pg/ml) | % Stimulated control | sem (%) | p$^{(1)}$ | % Relative inhibition | sem (%) | p$^{(1)}$ |
| Test compound | Concentration | | | | | | | | | |
| Non-stimulated control# | — | <39<br><39<br><39 | <39 | 0 | <0 | 0 | *** | 100 | 0 | *** |
| Stimulated conditions: PMA - 0.1 µg/ml  Control | — | 185876<br>216634<br>254805 | 219105 | 19936 | 100 | 9 | — | 0 | 9 | — |
| Indomethacin# | 10$^{-6}$ M | <39<br><39<br><39 | <39 | 0 | <0 | 0 | *** | >100 | 0 | *** |
| S-863 d | 0.004% | 171587<br>213634<br>246419 | 210547 | 21657 | 96 | 10 | ns | 4 | 10 | ns |
| | 0.02% | 162514<br>182307<br>200800 | 181874 | 11054 | 83 | 5 | ns | 17 | 5 | ns |
| | 0.1% | 115120<br>122952<br>152926 | 130333 | 11520 | 59 | 5 | * | 41 | 5 | * |
| S-863g | 0.00044% | 195605<br>116243<br>229545 | 180465 | 33572 | 82 | 15 | ns | 18 | 15 | ns |
| | 0.0013% | 178945<br>209944<br>219241 | 202710 | 12182 | 93 | 6 | ns | 7 | 6 | ns |
| | 0.004% | 147522<br>165184<br>208201 | 173636 | 18019 | 79 | 8 | ns | 21 | 8 | ns |

$^{(1)}$Threshold for statistical significance
ns: >0.05, Not significant
* 0.01 to 0.05, Significant
** 0.001 to 0.01, Very significant
*** <0.001, Extremely significant
< or >: Inferior or superior to the detection limit
<39.1 or >2500 pg/ml for non-diluted samples
<15640 or >1000000 pg/ml for diluted samples at 1/400
In case of values < or > to detection limits, ensuing calculations are extrapolated.
Non-diluted samples

Numbered Embodiments of the Disclosure

Notwithstanding the appended claims, the disclosure sets forth the following numbered embodiments:

1. A topical skin care composition comprising:
   (i) rose oil;
   (ii) cannabidiol (CBD), and
   (iii) a humectant,
   wherein the composition is delivered to skin by a cosmetic vehicle.
2. The topical skin care composition of embodiment 1, comprising up to about 5% rose oil and up to about 2% CBD.
3. The topical skin care composition of embodiments 1 and 2, comprising up to about 2% of a humectant.
4. The topical skin care composition of embodiment 3, wherein the humectant is selected from the group consisting of *Aloe vera* extract, glyceryl glucoside, and hyaluronic acid.
5. The topical skin care composition of embodiment 4, wherein the humectant is hyaluronic acid.
6. The topical skin care composition of embodiment 4, wherein the humectant is glyceryl glucoside.
7. The topical skin care composition of embodiment 1, wherein the rose oil is an extract of *Rhododendron ferrugineum*.
8. The topical skin care composition of embodiment 7, wherein the extract comprises stem cells.
9. The topical skin care composition of embodiment 1, wherein the rose oil is an extract of *Rosa damascena*.
10. The topical skin care composition of embodiment 1, wherein the cosmetic vehicle is selected from the group consisting of liposome, nanosome, oil-in-water emulsion, and water-in-oil emulsion.
11. The topical skin care composition of embodiment 1, wherein the cosmetic vehicle is a nanosome.
12. The topical skin care composition of embodiment 11, wherein the nanosome has an average particle size of 90 nm.
13. The topical skin care composition of embodiment 1, wherein the cosmetic vehicle is an oil-in-water emulsion.
14. The topical skin care composition of embodiment 1, wherein the cosmetic vehicle comprises up to about 60% glycerin, up to about 15% caprylic/capric triglycerides, and up to about 3% phospholipids.
15. A method of applying the topical skin care composition of embodiment 1 to skin, comprising topically applying the topical skin care composition of embodiment 1.

16. The method of embodiment 15, wherein the composition is applied to a face.
17. The method of embodiment 15, wherein the composition is applied to a wrinkle.
18. The method of embodiment 15, wherein the composition is applied to a fine line.
19. A method of reducing acne comprising applying the topical skin care composition of embodiment 1 to the skin.
20. The topical skin care composition of embodiment 1, wherein the composition is incorporated into a product selected from the group consisting of an eye cream, a serum, a face mask, and a lotion.
21. The topical skin care composition of embodiment 1, wherein the composition further comprises tocopherol.
22. The topical skin care composition of embodiment 1, comprising 2% v/v rose oil, 1% w/v CBD, 54% v/v glycerin, 1% v/v hyaluronic acid, 0.1% v/v tocopherol, 3% v/v phospholipids, and 10% v/v caprylic/capric triglycerides, wherein the rose oil is an extract from *Rhododendron ferrugineum*.
23. The topical skin care composition of embodiment 1, comprising 2% v/v rose oil, 1% v/v CBD, 54% v/v glycerin, 1% v/v hyaluronic acid, 0.1% v/v tocopherol, 3% v/v phospholipids, and 10% v/v caprylic/capric triglycerides, wherein the rose oil is an extract from *Rhododendron ferrugineum*.
24. The topical skin care composition of embodiment 1, comprising 2% v/v rose oil, 1% w/v CBD, 54% v/v glycerin, 1% v/v hyaluronic acid, 3% v/v phospholipids, and 10% v/v caprylic/capric triglycerides, wherein the rose oil is an extract from *Rhododendron ferrugineum*.
25. The topical skin care composition of embodiment 1, comprising 2% v/v rose oil, 1% v/v CBD, 54% v/v glycerin, 1% v/v hyaluronic acid, 3% v/v phospholipids, and 10% v/v caprylic/capric triglycerides, wherein the rose oil is an extract from *Rhododendron ferrugineum*.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Furthermore, International Application Publication No. WO 2008/010241A1, published Jan. 24, 2008, entitled: A Liposomal Complex of Sodium Carboxmethyl Beta-Glucan, is hereby incorporated by reference.

What is claimed is:
1. A topical skin care composition comprising:
(i) from about 0.5% w/w to about 5.0% w/w rose oil;
(ii) from about 1.0% w/w to about 5.0% w/w cannabidiol (CBD), and
(iii) glyceryl glucoside,
wherein the composition is formulated for delivery to skin by a cosmetic vehicle.
2. The topical skin care composition of claim 1, comprising about 2% w/w rose oil.
3. The topical skin care composition of claim 1, comprising up to about 1% w/w of glyceryl glucoside.
4. The topical skin care composition of claim 1, further comprising hyaluronic acid.
5. The topical skin care composition of claim 1, wherein the rose oil is an extract of *Rhododendron ferrugineum*.
6. The topical skin care composition of claim 5, wherein the extract comprises stem cells.
7. The topical skin care composition of claim 1, wherein the rose oil is an extract of *Rosa damascena*.
8. The topical skin care composition of claim 1, wherein the cosmetic vehicle is selected from the group consisting of liposome, nanosome, oil-in-water emulsion, and water-in-oil emulsion.
9. The topical skin care composition of claim 1, wherein the cosmetic vehicle is a nanosome.
10. The topical skin care composition of claim 9, wherein the nanosome has an average particle size of 90 nm.
11. The topical skin care composition of claim 1, wherein the cosmetic vehicle is an oil-in-water emulsion.
12. The topical skin care composition of claim 1, wherein the cosmetic vehicle comprises up to about 60% v/v glycerin, up to about 15% v/v caprylic/capric triglycerides, and up to about 3% v/v phospholipids.
13. The topical skin care composition of claim 1, comprising tocopherol.
14. A method of applying the topical skin care composition of claim 1 to skin, comprising topically applying the topical skin care composition of claim 1.
15. The method of claim 14, wherein the composition is applied to a face.
16. The method of claim 14, wherein the composition is applied to a wrinkle.
17. The method of claim 14, wherein the composition is applied to a fine line.
18. A method of reducing acne comprising applying the topical skin care composition of claim 1 to the skin.
19. The topical skin care composition of claim 1, wherein the composition is incorporated into a product selected from the group consisting of an eye cream, a serum, a face mask, and a lotion.
20. The topical skin care composition of claim 1, comprising 2% w/w rose oil, 1% w/w CBD, 54% w/w glycerin, 1% w/w glyceryl glucoside acid, 0.1% w/w tocopherol, 3% w/w phospholipids, and 10% w/w caprylic/capric triglycerides, wherein the rose oil is an extract from *Rhododendron ferrugineum*.
21. The topical skin care composition of claim 1, comprising 2% w/w rose oil, 1% w/w CBD, 54% w/w glycerin, 1% w/w glyceryl glucoside acid, 3% w/w phospholipids, and 10% w/w caprylic/capric triglycerides, wherein the rose oil is an extract from *Rhododendron ferrugineum*.
22. A topical skin care composition comprising:
(i) about 2.0% w/w rose oil;
(ii) about 1.0% w/w cannabidiol (CBD), and
(iii) about 1% glyceryl glucoside,
wherein the composition is formulated for delivery to skin by a cosmetic vehicle.
23. The topical skin care composition of claim 1, comprising about 1 w/w CBD.

* * * * *